US011020484B2

(12) United States Patent
Xiong et al.

(10) Patent No.: US 11,020,484 B2
(45) Date of Patent: Jun. 1, 2021

(54) BUFFERED FORMULATIONS OF EXENDIN (9-39)

(71) Applicants: Eiger BioPharmaceuticals, Inc., Palo Alto, CA (US); The Board of Trustees of the Leland Stanford Junior University, Stanford, CA (US)

(72) Inventors: Xiaofeng Xiong, Santa Clara, CA (US); Debra Odink, Oakland, CA (US); Colleen M. Craig, Burlingame, CA (US); Christine M. N. Smith, San Diego, CA (US); Tracey L. McLaughlin, Santa Clara, CA (US)

(73) Assignees: Eiger BioPharmaceuticals, Inc., Palo Alto, CA (US); The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 16/461,329

(22) PCT Filed: Nov. 21, 2017

(86) PCT No.: PCT/US2017/062838
§ 371 (c)(1),
(2) Date: May 15, 2019

(87) PCT Pub. No.: WO2018/094404
PCT Pub. Date: May 24, 2018

(65) Prior Publication Data
US 2020/0069802 A1    Mar. 5, 2020

Related U.S. Application Data

(60) Provisional application No. 62/424,979, filed on Nov. 21, 2016, provisional application No. 62/517,065, filed on Jun. 8, 2017.

(51) Int. Cl.
| | | |
|---|---|---|
| A61K 38/00 | (2006.01) | |
| A61K 47/12 | (2006.01) | |
| A61P 3/10 | (2006.01) | |
| A61K 9/00 | (2006.01) | |
| A61K 38/26 | (2006.01) | |
| A61K 47/26 | (2006.01) | |

(52) U.S. Cl.
CPC ............ *A61K 47/12* (2013.01); *A61K 9/0019* (2013.01); *A61K 38/26* (2013.01); *A61K 47/26* (2013.01); *A61P 3/10* (2018.01)

(58) Field of Classification Search
None
See application file for complete search history.

(56) References Cited

U.S. PATENT DOCUMENTS

| | | | |
|---|---|---|---|
| 5,424,286 A | 6/1995 | Eng | |
| 6,004,297 A | 12/1999 | Steenfeldt-Jensen et al. | |
| 6,268,343 B1 | 7/2001 | Knudsen et al. | |
| 6,458,924 B2 | 10/2002 | Knudsen et al. | |
| 6,469,021 B1 | 10/2002 | Truesdale et al. | |
| 6,479,065 B2 | 11/2002 | Jaworowicz et al. | |
| 6,495,164 B1 | 12/2002 | Ramstack et al. | |
| 6,573,291 B2 | 6/2003 | Gronberg et al. | |
| 6,667,061 B2 | 12/2003 | Ramstack et al. | |
| 6,824,822 B2 | 11/2004 | Rickey et al. | |
| 6,858,576 B1 | 2/2005 | Young et al. | |
| 6,872,700 B1 | 3/2005 | Young et al. | |
| 6,902,744 B1 | 6/2005 | Kolterman et al. | |
| 6,903,074 B1 | 6/2005 | Morgan et al. | |
| 6,956,026 B2 | 10/2005 | Beeley et al. | |
| 7,223,440 B2 | 5/2007 | Rickey et al. | |
| 7,235,627 B2 | 6/2007 | Knudson et al. | |
| 7,238,663 B2 * | 7/2007 | DeFelippis | ............... A61P 1/00 514/6.5 |
| 7,297,761 B2 | 11/2007 | Beeley et al. | |
| 7,456,254 B2 | 11/2008 | Wright et al. | |
| 7,521,423 B2 | 4/2009 | Young et al. | |
| 7,563,871 B2 | 7/2009 | Wright et al. | |
| 7,612,176 B2 | 11/2009 | Wright et al. | |
| 7,741,269 B2 | 6/2010 | Young et al. | |

(Continued)

FOREIGN PATENT DOCUMENTS

| | | |
|---|---|---|
| WO | 02-081649 A2 | 10/2002 |
| WO | 2008-085982 A2 | 7/2008 |

(Continued)

OTHER PUBLICATIONS

"Amidation", The Free Dictionary, available at https://www.thefreedictionary.com/Amidation, retrieved online on Nov. 21, 2019, 3 pages.

Alexopoulos K., et al, "Design and Synthesis of Novel Biologically Active Thrombin Receptor Non-Peptide Mimetics Based on the Pharmacophoric Cluster Phe/Arg/NH2 of the Ser42-Phe-Leu-Leu-Arg46 Motif Sequence: Platelet Aggregation and Relaxant Activities" J Med. Chem. vol. 47, Issue 13, DOI:10.1021/jm031080v, Jun. 17, 2004, p. 3338-52.

Andreasen, J.J., et al., "Secretion of Glucagon-Like Peptide-1 and Reactive Hypoglycemia after Partial Gastrectomy". Digestion, 1994. 55(4): p. 221-228.

(Continued)

*Primary Examiner* — Jeanette M Lieb
(74) *Attorney, Agent, or Firm* — Kilpatrick, Townsend & Stockton LLP

(57) ABSTRACT

Provided herein are liquid pharmaceutical formulations comprising exendin (9-39) or a pharmaceutically acceptable salt thereof and a tonicity modifier in a physiologically acceptable buffer having a pH in the range of about 5 to about 6. In some embodiments, the buffered liquid formulation comprises exendin (9-39) or a pharmaceutically acceptable salt thereof in an acetate buffer or a citrate buffer. Methods of treating or preventing hyperinsulinemic hypoglycemia in a subject comprising administering to the subject the buffered liquid formulation are also provided.

30 Claims, 19 Drawing Sheets

(56) References Cited

U.S. PATENT DOCUMENTS

| | | | |
|---|---|---|---|
| 8,076,288 | B2 | 12/2011 | Levy et al. |
| 8,114,833 | B2 | 2/2012 | Pedersen et al. |
| 8,216,180 | B2 | 7/2012 | Tschirren et al. |
| 8,268,781 | B2 | 9/2012 | Gotthardt et al. |
| 8,299,025 | B2 | 10/2012 | Alessi et al. |
| 8,329,648 | B2 | 12/2012 | Fineman et al. |
| 8,431,685 | B2 | 4/2013 | Wright et al. |
| 8,439,864 | B2 | 5/2013 | Galbraith et al. |
| 8,445,647 | B2 | 5/2013 | Prickett et al. |
| 8,461,105 | B2 | 6/2013 | Wright et al. |
| 8,546,326 | B2 | 10/2013 | Joabsson et al. |
| 8,846,612 | B2 | 9/2014 | Aprikian et al. |
| 8,895,033 | B2 | 11/2014 | Houchin et al. |
| 8,906,851 | B2 | 12/2014 | Fineman et al. |
| 8,969,293 | B2 | 3/2015 | Imran |
| 9,616,108 | B2 | 4/2017 | Stoffers et al. |
| 9,821,031 | B2 | 11/2017 | Stoffers et al. |
| 10,188,702 | B2 | 1/2019 | Stoffers et al. |
| 10,639,354 | B2 | 5/2020 | McLaughlin et al. |
| 10,653,753 | B2 | 5/2020 | Xiong |
| 10,660,937 | B2 | 5/2020 | McLaughlin et al. |
| 2002/0123461 | A1 | 9/2002 | Drucker et al. |
| 2004/0092443 | A1 | 5/2004 | Fridkin et al. |
| 2004/0116331 | A1 | 6/2004 | Seeley et al. |
| 2008/0269130 | A1 | 10/2008 | Stoffers et al. |
| 2010/0029554 | A1* | 2/2010 | Ghosh ............... A61P 5/50 514/1.1 |
| 2011/0124555 | A1 | 5/2011 | Schmid |
| 2013/0172250 | A1 | 7/2013 | Fineman et al. |
| 2013/0195939 | A1 | 8/2013 | Kidron |
| 2013/0252894 | A1 | 9/2013 | Kuzma et al. |
| 2014/0256626 | A1 | 9/2014 | Santi et al. |
| 2014/0309168 | A1 | 10/2014 | Rosendahl |
| 2015/0005233 | A1 | 1/2015 | DeFrees |
| 2015/0056285 | A1 | 2/2015 | Houchin et al. |
| 2015/0057227 | A1 | 2/2015 | Leung |
| 2015/0238568 | A1 | 8/2015 | Fineman et al. |
| 2015/0258016 | A1 | 9/2015 | Alessi et al. |
| 2015/0274800 | A1 | 10/2015 | Schellenberger et al. |
| 2015/0368311 | A1 | 12/2015 | Haack et al. |
| 2016/0185837 | A1 | 6/2016 | Bednarek et al. |
| 2018/0117122 | A1 | 5/2018 | McLaughlin et al. |
| 2018/0147261 | A1 | 5/2018 | McLaughlin et al. |
| 2019/0336584 | A1 | 11/2019 | Stoffers et al. |

FOREIGN PATENT DOCUMENTS

| | | |
|---|---|---|
| WO | 2011-109787 A1 | 9/2011 |
| WO | 2016/191394 A1 | 12/2016 |
| WO | 2016/191395 A1 | 12/2016 |
| WO | 2018/094404 A1 | 5/2018 |

OTHER PUBLICATIONS

Andronati, S.A. et al, "Peptidomimetics—Antagonists of the Fibrinogen Receptors: Molecular Design, Structures, Properties and Therapeutic Applications." Curr Med Chem 11(9): 1183-211, 2004.

Ashkenazi A., et al.,"Immunoadhesins". Int. Rev. Immunol., vol. 10, Issue 2-3, DOI:10.3109/08830189309061697, 1993, p. 219-227.

Bantle, J.P., et al., "Hyperinsulinemic Hypoglycemia Developing Late after Gastric Bypass", Obes Surg. vol. 17, https://doi.org/10.1007/s11695-007-9102-6, May 2007, p. 592-595.

Botros, N., et al., "Effect of Carbohydrate Restriction in Patients with Hyperinsulinemic Hypoglycemia after Roux-en-Y Gastric Bypass", Obes Surg. vol. 24, Issue 11, https://doi.org/10.1007/s11695-014-1319-6,Jun. 6, 2014, p. 1850-1855.

Breslin, M.J., et al, "Non-Peptide alphavbeta3 Antagonists. Part 6: Design and Synthesis of alphavbeta3 Antagonists Containing a Pyridone or Pyrazinone Central Scaffold". Bioorg & Med Chem Lett vol. 13, Issue 10, DOI: 10.1016/S0960-894X(03)00254-3, Jun. 2003, p. 1809-12.

Buchwald, H., et al., "Long term, continuous intravenous heparin administration by an implantable infusion pump in ambulatory patients with recurrent venous thrombosis", Surgery, DOI:https://doi.org/10.5555/uri:pii:0039606080901257, vol. 88, Issue 4, Oct. 1, 1980, p. 507-516.

Calabria, A.C., et al., "Postoperative Surveillance and Detection of Postprandial Hypoglycemia after Fundoplasty in Children", published in final edited form as J Pediatr. vol. 159, No. 4, doi:10/1016/j.jpeds.2011.03.049,597-601. Oct. 2011, 11 pages.

Calabria, A.C., et al., "GLP-1 Receptor Antagonist Exendin-(9-39) Elevates Fasting Blood Glucose Levels in Congenital Hyperinsulinism Owing to Inactivating Mutations in the ATP-Sensitive K+ Channel" Diabetes, vol. 61, No. 10, DOI:10.2337/db12-0166, Oct. 2012, 2585-2591.

Cancelas, J., et al., "Suppression by Exendin(9-39)amide of Glucagon-Like Peptide-1 Insulinotropic Action in Rats Infused with Dimethyl Ester of Succinic Acid", Endocrine, vol. 15, Issue 3, DOI:10.1385/ENDO:15:3:283, Aug. 2001, p. 283-5.

Cancelas, J., et al., "Resistance of Succinic Acid Dimethyl Ester Insulinotropic Action to Exendin (9-39) Amide", Hormone and Metabolic Research, vol. 34, No. 1, DOI:10.1055/s-2002-19960, Feb. 1, 2002, pp. 13-15.

Caudy, A.A., et al. "Fragile X-related protein and VIG associate with the RNA interference machinery", Genes & Development, vol. 16, No. 19, DOI:10.1101/gad.1025202, 2002, p. 2491-2496.

Cheon, H.G., et al., "High-affinity binding sites for related fibroblast growth factor ligands reside within different receptor immunoglobulin-like domains", Proceedings of the National Academy of Science, vol. 91, No. 3, DOI:10.1073/pnas.91.3.989, Feb. 1994, pp. 989-993.

Cosgrove, K.E., et al., "BPDZ 154 Activates Adenosine 5'-Triphosphate-Sensitive Potassium Channels: In Vitro Studies Using Rodent Insulin-Secreting Cells and Islets Isolated from Patients with Hyperinsulinism", The Journal of Clinical Endocrinology and Metabolism, vol. 87, No. 11, DOI:https://doi.org/10.1210/jc.2002-020439, Nov. 1, 2002, 4860-4868.

Craig, C.M., et al., "Efficacy and pharmacokinetics of subcutaneous exendin (9-39) in patients with post-bariatric hypoglycaemia", Diabetes, Obesity and Metabolism, vol. 20, Issue 2, DOI:https://doi.org/10.1111/dom.13078, 2017, p. 1-10.

De Leon, D.D., "Effect of Exendin-(9-38) on Glycemic Control in Subjects With Congenital Hyperinsulinism", U.S. National Library of Medicine, ClinicalTrials.gov, retrieved on Nov. 21, 2019 from https://www.clinicaltrials.gov/ct2/show/NCT00571324, 28 pages.

De Leon, D.D., et al. "Exendin-(9-39) Corrects Fasting Hypoglycemia in SUR-1 / Mice by Lowering cAMP in Pancreatic beta-cells and Inhibiting Insulin Secretion" Journal of Biological Chemistry, vol. 283, Issue 38, DOI:10.1074/jbc.M804372200, Sep. 19, 2008, 24 pages.

De Leon, D.D., et al. "Role of Endogenous Glucagon-Like Peptide-1 in Islet Regeneration After Partial Pancreatectomy", Diabetes, vol. 52, DOI:https://doi.org/10.2337/diabetes.52.2.365, Feb. 2003, p. 365-371.

Deary, I.J., et al. "Partitioning the symptoms of hypoglycaemia using multi-sample confirmatory factor analysis", Diabetologia, vol. 35, Issue 8, DOI:https://doi.org/10.1007/BF00401150, 1993, p. 771-777.

Drucker, D.J., et al. "Biologic actions and therapeutic potential of the proglucagon-derived peptides", Nature Clinical Practice Endocrinology & Metabolism, vol. 1, No. 1, DOI:10.1038/ncpendmet0017, Nov. 2005, p. 22-31.

Dunne, M.J., et al. "Hyperinsulinism in Infancy: From Basic Science to Clinical Disease", Physiological Reviews, vol. 84, No. 1,DOI:10.1152/physrev.00022.2003, Jan. 2004, p. 239-275.

Edwards, C.M., et al. "Glucagon-like peptide 1 has a physiological role in the control of postprandial glucose in humans: studies with the antagonist exendin 9-39", Diabetes, vol. 48, No. 1, DOI:https://doi.org/10.2337/diabetes.48.1.86, Jan. 1999, p. 86-93.

Edwards, C.M., et al., "Subcutaneous glucagon-like peptide-1 (7-36) amide is insulinotropic and can cause hypoglycaemia in fasted healthy subjects", Clin Sci (Lond), vol. 95, No. 6, DOI:https://doi.org/10.1042/cs0950719, Dec. 1, 1998, p. 719-724.

Eliasson, L., et al. "SUR1 Regulates PKA-independent cAMP-induced Granule Priming in Mouse Pancreatic B-Cells", J. Gen. Physiol, vol. 121, No. 3, DOI:10.1085/jgp.20028707, Mar. 2003, p. 181-197.

* cited by examiner

(56) References Cited

OTHER PUBLICATIONS

Eng, J., et al. "Isolation and Characterization of Exendin-4, an Exendin-3 Analogue, from Heloderma suspectum Venom: Further evidence for an exendin receptor on dispersed acini from guinea pig pancreas", The Journal of Biological Chemistry, vol. 267, No. 11, Apr. 15, 1992, p. 7402-7405.

Evan, G.I., et al., "Isolation of Monoclonal Antibodies Specific for Human c-myc Proto-Oncogene Product", Molecular and Cellular Biology, vol. 5, No. 12, Dec. 1985, p. 3610-3616.

Extended European Search Report dated Aug. 30, 2011 in European Application No. 08713063.9, 5 pages.

Extended European Search Report dated Dec. 1, 2014 in European Application No. 14171762.9, 6 pages.

Extended European Search Report dated Jan. 21, 2019 in European Application No. 18201976.0, 6 pages.

Field, J., et al., "Purification of a RAS-responsive Adenylyl Cyclase Complex from *Saccharomyces cerevisiae* by Use of an Epitope Addition Method", Molecular and Cellular Biology, vol. 8, No. 5, DOI:10.1128/mcb.8.5.2159, May 1988, p. 2159-2165.

Final Office action dated Oct. 23, 2019 in U.S. Appl. No. 15/576,647, 12 pages.

Final Office action dated Sep. 25, 2019 in U.S. Appl. No. 15/576,647, 16 pages.

Fournet, J.C., et al., "Unbalanced Expression of 11p15 Imprinted Genes in Focal Forms of Congenital Hyperinsulinism", The Amercian Journal of Pathology, vol. 158, No. 6, Jun. 2001, DOI:https://doi.org/10.1016/S0002-9440(10)64689-5, p. 2177-2184.

Gebhard, B., et al., "Postprandial GLP-1, Norepinephrine, and Reactive Hypoglycemia in Dumping Syndrome", Digestive Diseases and Sciences, vol. 46, Issue 9, DOI:https://doi.org/10.1023/A:1010635131228, Sep. 2001, p. 1915-1923.

Goodson, J.M., Chapter 6 "Dental Applications" in: Medical Applications of Controlled Release, 1984, vol. 2, p. 116-138.

Heber, D., et al., "Endocrine and nutritional management of the post-bariatric surgery patient: an Endocrine Society Clinical Practice Guideline", J Clin Endocrinol Metab. vol. 95, Issue 11, DOI:10.1210/jc.2009-2128, Nov. 2010, p. 4823-4843.

Heidaran, M.A., et al., "Beta PDGFR-IgG chimera demonstrates that human beta PDGFR Ig-like domains 1 to 3 are sufficient for high affinity PDGF BB binding", The FASEB Journal, vol. 9, No. 1, DOI:https://doi.org/10.1096/fasebj.9.1.7821753, Jan. 1, 1995, p. 140-145.

Hepburn, D.A., et al., "Symptoms of acute insulin-induced hypoglycaemia in humans with and without IDDM", Diabetes Care, vol. 14, No. 11, DOI:https://doi.org/10.2337/diacare.14.11.949, Nov. 1991, p. 949-957.

Hofeldt, F.D., "Reactive hypoglycemia", Endocrinology and Metabolism Clinics of North America, vol. 18, No. 1, Mar. 1989, p. 185-201.

Hopp, T.P., et al., "A Short Polypeptide Marker Sequence Useful for Recombinant Protein Identification and Purification", Bio/Technology, vol. 6, No. 10, DOI:10.1038/nbt1088-1204, Oct. 1988, p. 1204-1210.

Hussain, K., et al., "Medications used in the treatment of hypoglycemia due to congenital hyperinsulinism of infancy (HI)", Pediatric Endocrinology Reviews, vol. 2, Supplement 1, Nov. 2004, p. 163-167.

International Hypoglycaemia Study Group (IHSG), Amiel, S.A., et al., "Glucose concentrations of less than 3.0 mmol/L (54 mg/dL) should be reported in clinical trials: A joint position statement of the American Diabetes Association and the European Association for the Study of Diabetes", Diabetes Care, vol. 40, DOI:10.2337/dc16/2215, Jan. 2017, p. 155-157.

International Search Report and Written Opinion dated May 26, 2017 in International Patent Application No. PCT/US2017/020596, 10 pages.

International Search Report and Written Opinion dated Sep. 19, 2008 in International Patent Application No. PCT/US2008/000281, filed Jan. 8, 2008, 8 pages.

Kellogg, T.A., et al., "Postgastric bypass hyperinsulinemic hypoglycemia syndrome: characterization and response to a modified diet", Surgery for Obesity and Related Diseases, vol. 4, Issue 4, DOI:10.1016/j.soard.2008.05.005, Jul.-Aug. 2008, p. 492-499.

Kenny, C., "When Hypoclycemia is not obvious: diagnosing and treating under-recognized and undisclosed hypoglycemia", Primary Care Diabetes, vol. 8, Issue 1, DOI:http://dx.doi.org/10.1016/j.pcd.2013.09.002, Apr. 1, 2014, p. 3-11.

Kim, S.H., et al., "Glucose-stimulated insulin secretion in gastric bypass patients with hypoglycemic syndrome: no evidence for inappropriate pancreatic beta-cell function", Obesity Surgery, vol. 20, Issue 8, DOI:https://doi.org/10.1007/s11695-010-0183-2, Aug. 2010, p. 1110-1116.

Koh, T.H., et al., "Neonatal hypoglycaemia—the controversy regarding definition", Archives of Disease in Childhood, vol. 63, No. 11, DOI:10.1136/adc.63.11.1386, Nov. 1988, p. 1386-1388.

Kulkarni, R.N., et al., "Use of Exendin (9-39) Amide to define the in-vivo and in-vitro roles of GLP-1 (7-36) Amide in the regulation of Insulin secretion", Regulatory Peptides, vol. 57, No. 2, May 1995, p. 201.

Laferrere, B., et al., "Effect of weight loss by gastric bypass surgery versus hypocaloric diet on glucose and incretin levels in patients with type 2 diabetes", The Journal of Clinical Endocrinology & Metabolism, vol. 93, Issue 7, DOI:https://doi.org/10.1210/jc.2007-2851, Jul. 2008, p. 2479-2485.

Langer, R., "New Methods of Drug Delivery", Science, vol. 249, Issue 4976, DOI:10.1126/science.2218494, Sep. 28, 1990, p. 1527-1533.

Larochelle, W.J., et al., "Specific Receptor Detection by a Functional Keratinocyte Growth Factor-Immunoglobulin Chimera", The Journal of Cell Biology, vol. 129, No. 2, DOI:https://doi.org/10.1083/jcb.129.2.357, Apr. 15, 1995, p. 357-366.

Larraufie, P., et al., "Important Role of the GLP-1 Axis for Glucose Homeostasis after Bariatric Surgery", Cell Reports, DOI:https://doi.org/10.1016/j.celrep.2019.01.047, vol. 26, Issue 6, Feb. 5, 2019, p. 1399-1408.

Lev-Ran, A., et al., "The diagnosis of postprandial hypoglycemia", Diabetes, vol. 30, Issue 12, DOI:10.2337/diab.30.12.996, Dec. 1981, p. 996-999.

Lutz-Freyermuth, C., et al., "Quantitative determination that one of two potential RNA-binding domains of the a protein component of the U1 small nuclear ribonucleoprotein complex binds with high affinity to stem-loop II of U1 RNA", Proceedings of the National Academy of Sciences of the United States of America, vol. 87, Issue 16, DOI:10.1073/pnas.87.16.6393, Aug. 1990, p. 6393-6397.

Mandal, A., "Defining Hypoglycemia", News Medical: Life Sciences, retrieved on Nov. 20, 2019 from https://www.news-medicatnet/health/Defining-Hypoglycemia.aspx, 3 pages.

Martin, G.A., et al., "GAP domains responsible for ras p21-dependent inhibition of muscarinic atrial K+ channel currents", Science, vol. 255, Issue 5041, DOI:10.1126/science.1553544, Jan. 10, 1992, p. 192-194.

Mechanick, J.I., et al., "Clinical practice guidelines for the perioperative nutritional, metabolic, and nonsurgical support of the bariatric surgery patient-2013 update: cosponsored by American Association of Clinical Endocrinologists", Obesity (Silver Spring), vol. 21, Issue 1, DOI:10.1002/oby.20461, Mar. 2013, 64 pages.

Meier et al., "Comment to: Patti ME, McMahon G, Mun EC et al. (2005) Severe hypoglycaemia post-gastric bypass requiring partial pancreatectomy: evidence for inappropriate insulin secretion and pancreatic islet hyperplasia. Diabetologia 49:2236-2240", Diabetologia, vol. 49, Issue 3, DOI:10.1007/s00125-005-0114-2, Mar. 2006, p. 607-608.

Meijeren, J.V., et al., "Evaluation of carbohydrate restriction as primary treatment for post-gastric bypass hypoglycemia", Surgery for Obesity and Related Diseases, vol. 13, Issue 3, DOI:https://doi.org/10.1016/j.soard.2016.11.004, Mar. 2017, p. 404-410.

Miholic, J., et al. "Emptying of the Gastric Substitute, Glucagon-like peptide-1 (GLP-1), and Reactive Hypoglycemia After Total Gastrectomy", Digestive Diseases and Sciences, vol. 36, No. 10, DOI:https://doi.org/10.1007/BF01296800, Oct. 1991, p. 1361-1370.

(56) References Cited

OTHER PUBLICATIONS

Moize, V.L., et al., "Nutritional pyramid for post-gastric bypass patients", Obesity Surgery, vol. 20, Issue 8, DOI:10.1007/s11695-010-0160-9, 2010, p. 1133-1141.

Naz, R.K, et al., "Novel human prostate-specific cDNA: molecular cloning, expression, and immunobiology of the recombinant protein", Biochemical and Biophysical Research Communications, vol. 297, Issue 5, DOI:https://doi.org/10.1016/S0006-291X(02)02349-5, Oct. 11, 2002, p. 1075-1084.

Ng, D.D., et al. 'Acarbose treatment of postprandial hypoglycemia in children after Nissen fundoplication', The Journal of Pediatrics, vol. 139, Issue 6, DOI:https://doi.org/10.1067/mpd.2001.119169, Dec. 2001, p. 877-879.

Nielsen, P.E., "Peptide nucleic acids as therapeutic agents", Current Opinion in Structural Biology, vol. 9, Issue 3, DOI: https://doi.org/10.1016/50959-440X(99)80047-5, Jun. 1999, p. 353-357.

Non-Final Office action dated Mar. 21, 2019 in U.S. Appl. No. 15/576,647, 17 pages.

Paborsky, L.R., et al., "Mammalian cell transient expression of tissue factor for the production of antigen", Protein Engineering, Design and Selection, vol. 3, Issue 6, DOI:https://doi.org/10.1093/protein/3.6.547, May 1990, p. 547-553.

Palladino, A.A., et al., "Hyperinsulinism in Infancy and Childhood: When an Insulin Level is Not Always Enough", Clinical Chemistry, vol. 54, Issue 2, DOI:10.1373/clinchem.2007.098988, Jan. 2008, p. 256-263.

Patti, M.E., et al., "Severe hypoglycemia postgastric bypass requiring partial pancreatectomy: evidence for inappropriate insulin secretion and pancreatic islet hyperplasia", Diabetologia, vol. 48, Issue 11, DOI:10.1007/500125-005-1933-x , 2005, p. 2236-2240.

Saudek, C.D., et al., "A Preliminary Trial of the Programmable Implantable Medication System for Insulin Delivery", The New England Journal of Medicine, vol. 321, No. 9, DOI: 10.1056/NEJM198908313210904, Aug. 31, 1989, p. 574-579.

Schirra, J., et al., "Endogenous glucagon-like peptide 1 controls endocrine pancreatic secretion and antro-pyloro-duodenal motility in humans", Gut, vol. 55, Issue 2, DOI:10.1136/gut.2004.059741, Feb. 2006, p. 243-251.

Schirra, J., et al., "Exendin(9-39)amide Is an Antagonist of Glucagon-like Peptide-1(7-36)amide in Humans", The Journal of Clinical Investigation, vol. 101, No. 7, DOI:https://doi.org/10.1172/JC11349, Apr. 1, 1998, p. 1421-1430.

Scroochi, L.A., et al., "Glucose intolerance but normal satiety in mice with a null mutation in the glucagon-like peptide 1 receptor gene", Nature Medicine, vol. 2, No. 11, DOI:https://doi.org/10.1038/nm1196-1254, Nov. 1, 1996, p. 1254-1258.

Seaquist, E.R., et al., "Hypoglycemia and Diabetes: A Report of a Workgroup of the American Diabetes Association and the Endocrine Society", Diabetes Care, vol. 36, Issue 5, DOI:https://doi.org/10.2337/dc12-2480 , May 2013, p. 1384-1395.

Seghers, V., et al. "Sur 1 Knockout Mice. A Model for KATP Channel-Independent Regulation of Insulin Secretion", The Journal of Biological Chemistry, vol. 275, No. 13, DOI:10.1074/jbc.275.13.9270, Mar. 31, 2000, p. 9270-9277.

Sefton, M.V., "Implantable Pumps" Critical Reviews in Biomedical Engineering, vol. 14, Issue 3 , p. 201-240.

Service, F.J., et al., "Mean Amplitude of Glycemic Excursions, a Measure of Diabetic Instability", Diabetes, vol. 19, Issue 9, DOI:https://doi.org/10.2337/diab.19.9.644, Sep. 1970, p. 644-655.

Service, G.J., et al., "Hyperinsulinemic hypoglycemia with nesidioblastosis after gastric-bypass surgery", The New England Journal of Medicine, vol. 353, Issue 3, DOI:10.1056/NEJMoa043690, Jul. 21, 2005, p. 249-254.

Skinner, R.H., et al., "Use of the Glu-Glu-Phe C-terminal Epitope for Rapid Purification of the Catalytic Domain of Normal and Mutant ras GTPase-activating Proteins", The Journal of Biological Chemistry, vol. 266, No. 22, Issue of Aug. 5, 1991, p. 14163-14166.

Song, J., et al, "NMR for the design of functional mimetics of protein-protein interactions: one key is in the building of bridges", Biochemistry and Cell Biology, vol. 76, Issue 2-3, DOI:10.1139/bcb-76-2-3-177, 1998, p. 177-188.

Stanley, C.A., et al., "Editorial: Advances in Diagnosis and Treatment of Hyperinsulinism in Infants and Children", The Journal of Clinical Endocrinology & Metabolism, vol. 87, Issue 11, DOI:10.1210/jc.2002-021403, Nov. 2002, p. 4857-4859.

Suhl, E., et al., "Medical nutrition therapy for post-bariatric hypoglycemia: practical insights", Surgery for Obesity and Related Diseases, vol. 13, Issue 5, DOI:10.1016/j.soard.2017.01.025, May 2017, p. 888-896.

Tack, J., et al., "Pathophysiology, diagnosis and management of postoperative dumping syndrome", Nature Reviews Gastroenterology & Hepatology, vol. 6, Issue 10, DOI:https://doi.org/10.1038/nrgastro.2009.148, Sep. 1, 2009, p. 583-590.

Tan, M.J., et al., "Repeat subcutaneous dosing of exendin 9-39 reduces hyperinsulinemic hypoglycemia and neuroglycopenic symptoms in patients with post-bariatric hypoglycemia", Poster presentation at the American Diabetes Association's 77th Scientific Sessions, San Diego, CA, Jun. 9-13, 2017, 1 page.

Thanthan, S., et al., "Glucagon-like peptide-1 inhibits insulinotropic effects of oxyntomodulin and glucagon in cattle", Domestic Animal Endocrinology, vol. 42, Issue 3, DOI:https://doi.org/10.1016/j.domaniend.2011.11.004, Apr. 2012, p. 155-164.

Todd, J.F., et al., "A tumor that secretes glucagon-like peptide-1 and somatostatin in a patient with reactive hypoglycemia and diabetes", The Lancet, vol. 361, Issue 9353, DOI:https://dotorg/10.1016/50140-6736(03)12256-8, Jan. 18, 2003, p. 228-230.

Toft-Nielsen, M., et al., "Exaggerated secretion of glucagon-like peptide-1 (GLP-1) could cause reactive hypoglycaemia", Diabetologia, vol. 41, Issue 10, DOI:https://dotorg/10.1007/s001250051049, 1998, p. 1180-1186.

Toft-Nielsen, M.-B., et al. , "Determinants of the Effectiveness of Glucagon-Like Peptide-1 in Type 2 Diabetes", The Journal of Clinical Endocrinology & Metabolism, vol. 86, Issue 8, DOI:https://doi.org/10.1210/jcem.86.8.7743, Aug. 1, 2001, p. 3853-3860.

Vilsboll T., et al., No reactive hypoglycaemia in Type 2 diabetic patients after subcutaneous administration of GLP-1 and intravenous glucose Diabet Medicine, vol. 18, Issue 2, DOI:https://doi.org/10.1046/j.1464-5491.2001.00424.x, Dec. 20, 2001, p. 144-149.

Vogt, A., et al, "A Non-peptide Mimetic of Ras-CAAX: selective Inhibition of Farnesyltransferase and Ras Processing", The Journal of Biological Chemistry, vol. 270, No. 2, DOI:https://doi.org/10.1074/jbc.270.2.660, Issue of Jan. 13, 1995, pp. 660-664.

Webb, M., et al., "Growth restriction and exendin 4 promote endocrine expression in cultured islet cells derived from patients with persistent hyperinsulinemic hypoglycemia of infancy (PHHI)", Endocrine Research, vol. 31, Issue 2, DOI:10.1080/07435800500229235, 2005, p. 99-109.

Chen, T., et al., "Interspecies Modeling and Prediction of Human Exenatide Pharmacokinetics", Pharm Res., vol. 30, No. 3, DOI:10.1007/s11095-012-0917-z, Mar. 2013, p. 751-760.

Cryer, P.E., et al., "Evaluation and management of adult hypoglycemic disorders: An Endocrine Society Clinical Practice Guideline", Journal of Clinical Endocrinology and Metabolism, vol. 94, Issue 3, DOI:10.1210/jc.2008-1410, Mar. 2009, p. 709-728.

De Leon, D.D., et al., "Determination of insulin for the diagnosis of hyperinsulinemic hypoglycemia", Best Practice & Research Clinical Endocrinology & Metabolism, vol. 27, Issue 6, DOI:https://doi.org/10.1016/j.beem.2013.06.005, Dec. 2013, p. 763-769.

Gardiner, S., et al., "Mesenteric Vasoconstriction and Hindquarters Vasodilatation Accompany the Pressor Actions of Exendin-4 in Conscious Rats", Journal of Pharmacology and Experimental Therapeutics, vol. 316, No. 2, DOI:https://doi.org/10.1124/jpet.105.093104, Feb. 2006, p. 852-859.

International Preliminary Report on Patentability dated Nov. 28, 2017 in International Patent Application No. PCT/US2016/033836, 11 pages.

International Preliminary Report on Patentability dated Nov. 28, 2017 in International Patent Application No. PCT/US2016/033837, 5 pages.

Kielgast, U., et al. "Antidiabetic Actions of Endogenous and Exogenous GLP-1 in Type 1 Diabetic Patients With and Without Residual

(56) References Cited

OTHER PUBLICATIONS

β-Cell Function", Diabetes, vol. 60, Issue 5, DOI:https://doi.org/10.2337/db10-1790, May 2011, p. 1599-1607.

Kumareswaran, K., et al. "Closed-loop Insulin Delivery: Towards Improved Diabetes Care", Discovery Medicine, vol. 13, No. 63, Feb. 23, 2012, p. 159-170.

Lasaosa, M., et al. "A liquid chromatography-mass spectrometry assay for quantification of Exendin[9-39] in human plasma", J Chromatogr B Analyt Technol Biomed Life Sci, vol. 0, DOI:10.1016/j.jchromb.2013.12.010, Feb. 1, 2014, p. 186-191.

Myint, K.S., et al., "Prolonged successful therapy for hyperinsulinaemic hypoglycaemia after gastric bypass: the pathophysiological role of GLP1 and its response to a somatostatin analogue", European Journal of Endocrinology, vol. 166, Issue 5, DOI:https://doi.org/10.1530/EJE-11-1065, May 2012, p. 951-955.

Calabria, A. et al. "Postprandial Hypoglycemia in Children After Gastric Surgery: Clinical Characterization and Pathophysiology." Hormone Research in Paediatrics. vol. 85, No. 2. Published Mar. 2016. pp. 140-146.

Coryell, W. "Depressive Disorders," Merck Manuals. Last full review/revision May 2018. Retrieved from the internet on May 14, 2019. Retrieved from the Internet: URL <https://www.merckmanuals.com/professional/psychiatric-disorders/mood-disorders/depressive-disorders>. 10 pages.

Craig, C. et al. "Critical Role for GLP-1 in Symptomatic Post-Bariatric Hypoglycaemia." Diabetologia, vol. 60, No. 3. Published Mar. 2017. pp. 531-540.

Davidson, M. et al. "Exenatide." Nature Review Drug Discover, vol. 4. Published Sep. 2005. pp. 713-714.

Eisenberg, D. et al. "ASMBS Position Statement on Postprandial Hyperinsulinemic Hypoglycemia after Bariatric Surgery." Surgery for Obesity and Related Diseases, vol. 13, Issue 3. Published Mar. 2017. pp. 371-378.

Extended European Search Report received in European Patent Application No. 16800620.3, dated Nov. 28, 2018. 5 pages.

Extended European Search Report received in European Patent Application No. 16800621.1, dated Mar. 9, 2018. 4 pages.

Office Action received in European Patent Application No. 16800621.1 dated Feb. 22, 2019. 3 pages.

Franco, J. et al., "A Review of Studies Comparing Three Laparoscopic Procedures in Bariatric Surgery: Sleeve Gastrectomy, Roux-en-Y Gastric Bypass and Adjustable Gastric Banding," Obesity Surgery, vol. 21, Issue 9. Published Sep. 2011. pp. 1458-1468.

Goldfine, A. et al. "Patients with Neuroglycopenia after Gastric Bypass Surgery Have Exaggerated Incretin and Insulin Secretory Responses to a Mixed Meal." The Journal of Clinical Endocrinology & Metabolism, vol. 92, Issue 12. Published 2007. pp. 4678-4685.

Gough, S. "Liraglutide: from clinical trials to clinical practice," Diabetes, Obesity and Metabolism, vol. 14, Supplement 2. Published Apr. 2012. pp. 33-40.

International Search Report and Written Opinion received in International Patent Application No. PCT/US2016/033836, dated Aug. 19, 2016. 13 pages.

International Search Report and Written Opinion received in International Patent Application No. PCT/US2016/033837, dated Aug. 18, 2016. 7 pages.

International Search Report and Written Opinion received in International Patent Application No. PCT/US2017/062838, dated Jan. 23, 2018. 8 pages.

International Preliminary Report on Patentability for PCT/US2017/062838 dated May 21, 2019, all pages.

Kapoor, R. et al., "Advances in the Diagnosis and Management of Hyperinsulinemic Hypoglycemia." Nature Clinical Practice Endocrinoloogy & Metabolism, vol. 5, Issue 3. Published Feb. 2009. pp. 101-112.

Langa, K. et al. "The Diagnosis and Management of Mild Cognitive Impairment: A Clinical Review," JAMA, vol. 312, Issue 23. Published Dec. 2014. pp. 2551-2561.

Manning, S. et al. "GLP-1: A Mediator of the Beneficial Metabolic Effects of Bariatric Surgery?" Physiology, vol. 30, No. 1. Published Jan. 2015. 28 pages.

Mclaughlin, T. et al. "Reversible Hyperinsulinemic Hypoglycemia after Gastric Bypass: A Consequence of Altered Nutrient Delivery." Journal of Clinical Endocrinology and Metabolism, vol. 95, No. 4. Published Apr. 2010. pp. 1851-1855.

Montrose-Rafizadeh, C. et al. "High Potency Antagonists of the Pancreatic Glucagon-like Peptide-1 Receptor." Journal of Biological Chemistry, vol. 272, Issue 34. Published Aug. 1997. pp. 21201-21206.

Nabel, E. "Cardiovascular Disease," New England Journal of Medicine, vol. 349, Issue 6. Published Jul. 2003. pp. 60-72.

Palladino, A. et al. "Increased Glucagon-Like Peptide-1 Secretion and Postprandial Hypoglycemia in Children after Nissen Fundoplication." Journal of Clinical Endocrinology and Metabolism, vol. 94, No. 1. Published Jan. 2009. pp. 39-44.

Patti, M. et al., "Hypoglycemia after Gastric Bypass: The Dark Side of GLP-1." Gastroenterology, vol. 146, No. 3. Published Mar. 2014. pp. 605-608.

Pramanick, S. et al. "Excipient Selection in Parenteral Formulation Development." Pharma Times, vol. 45, No. 3. Published Mar. 2013. pp. 65-77.

Salehi, M. et al., "Gastric Bypass Surgery Enhances Glucagon-Like Peptide 1-Stimulated Postprandial Insulin Secretion in Humans." Diabetes, vol. 60. No. 9. Published Sep. 2011. pp. 2308-2314.

Salehi, M. et al., "Blockade of Glucagon-like Peptide 1 Receptor Corrects Postprandial Hypoglycemia After Gastric Bypass." Gastroenterology, vol. 143, No. 3. Published Mar. 2014. pp. 669-680.

Traina, A. et al., "Primer on Pramlintide, an Amylin Analog," American Association of Diabetes Educators, vol. 37, No. 3. Published Apr. 2011. pp. 426-431.

Willard, F. et al. "Small Molecule Allosteric Modulation of the Glucagon-Like Peptide-1 Receptor Enhances the Insulinotropic Effect of Oxyntomodulin." Molecular Pharmacology, vol. 82, No. 6. Published Dec. 2012. pp. 1066-1073.

Lee, et al. "OR20-5 28-Day Dosing with Avexitide Improves Hyperinsulinemic Hypoglycemia in Patients with Severe, Refractory Post-Bariatric Hypoglycemia: The PREVENT Study", Journal of the Endocrine Society, vol. 3, Issue Supplement 1, DOI:10.1210/js.2019-OR20-5, Apr. 30, 2019, pp. 1-5.

International Search Report and Written Opinion dated Jan. 15, 2020 in International Patent Application No. PCT/US2019/056278, 26 pages.

Jezek, J., et al., "Biopharmaceutical formulations for pre-filled delivery devices", Expert opinion on drug delivery, vol. 10, Issue 6, DOI:10.1517/17425247.2013.780023, (2013): 811-828.

National Center for Biotechnology Information. "PubChem Compound Summary for CID 129012199, Exendin (9-39)" PubChem, Available from: https://pubchem.ncbi.nlm.nih.gov/compound/Exendin-_9-39. Accessed Sep. 26, 2020, pp. 1-36.

Pai, M. P., "Drug dosing based on weight and body surface area: mathematical assumptions and limitations in obese adults", Pharmacotherapy, vol. 32, Issue 9, DOI:10.1002/j.1875-9114.2012.01108.x, (2012): 856-868.

* cited by examiner

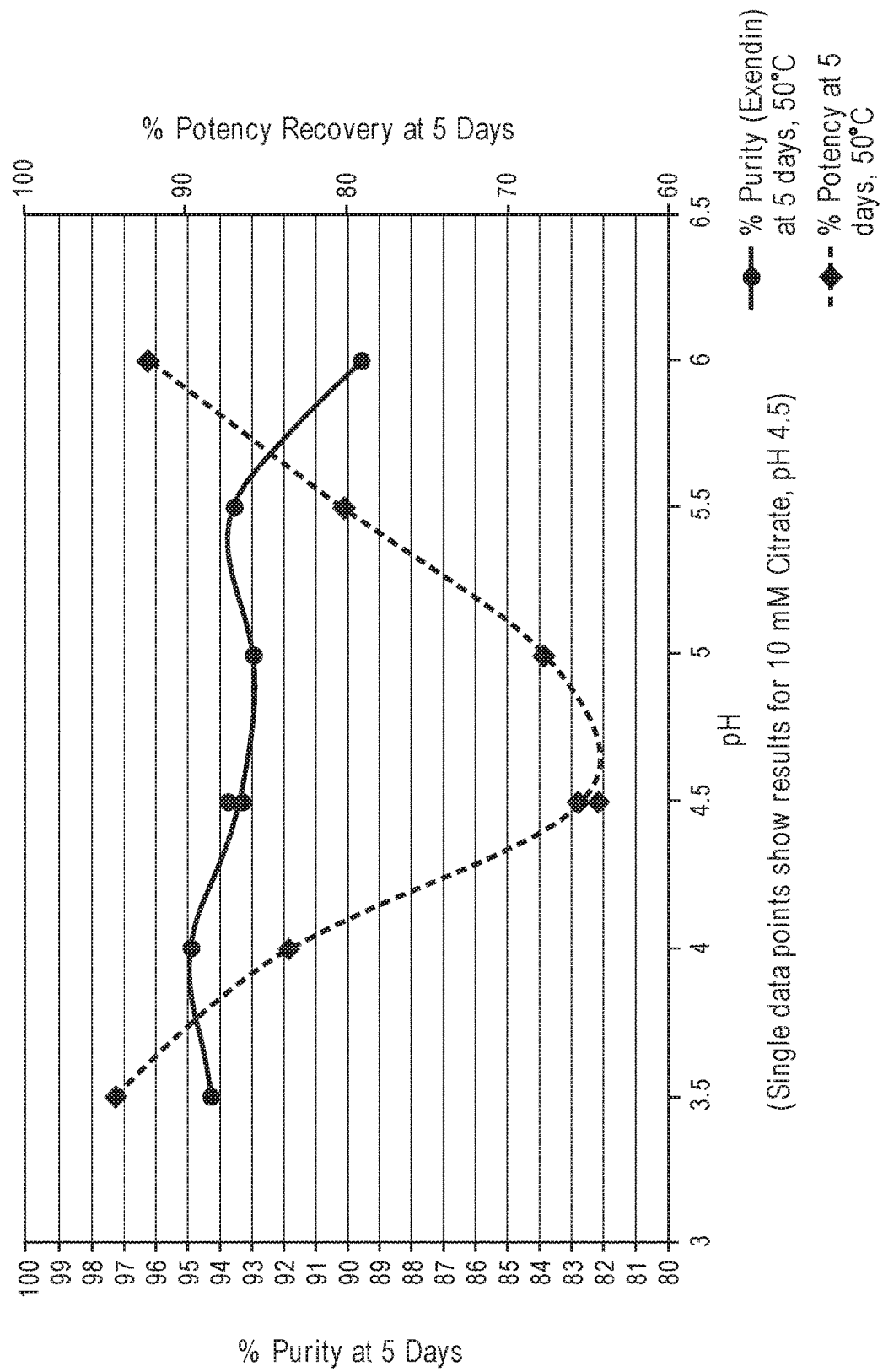

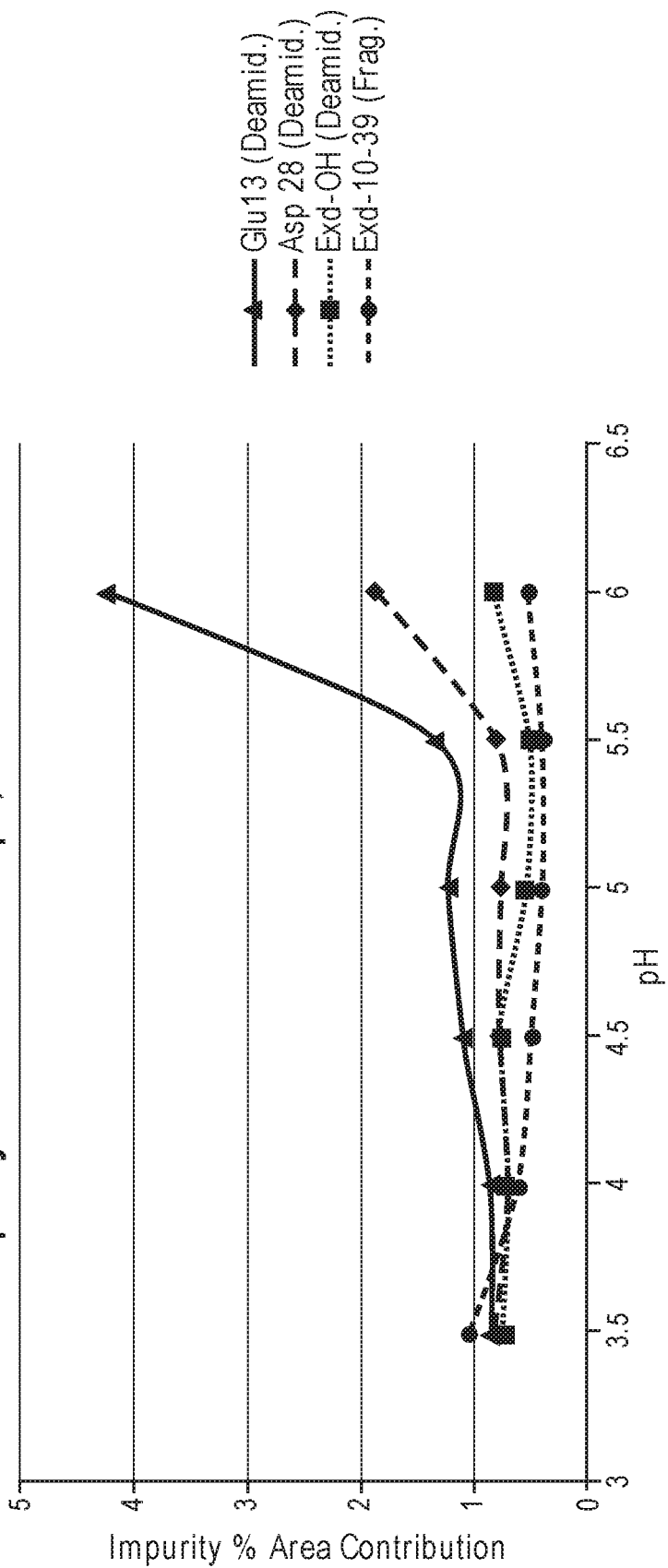

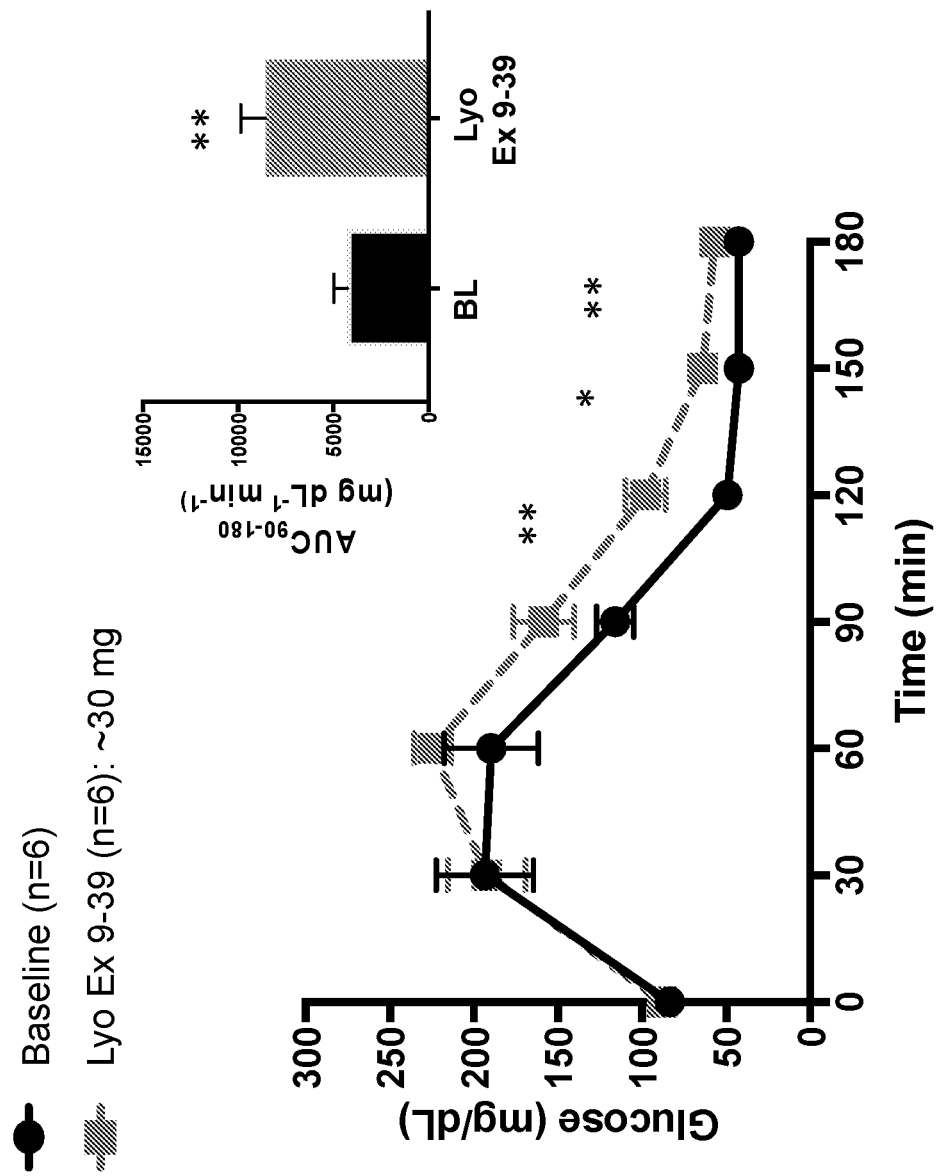

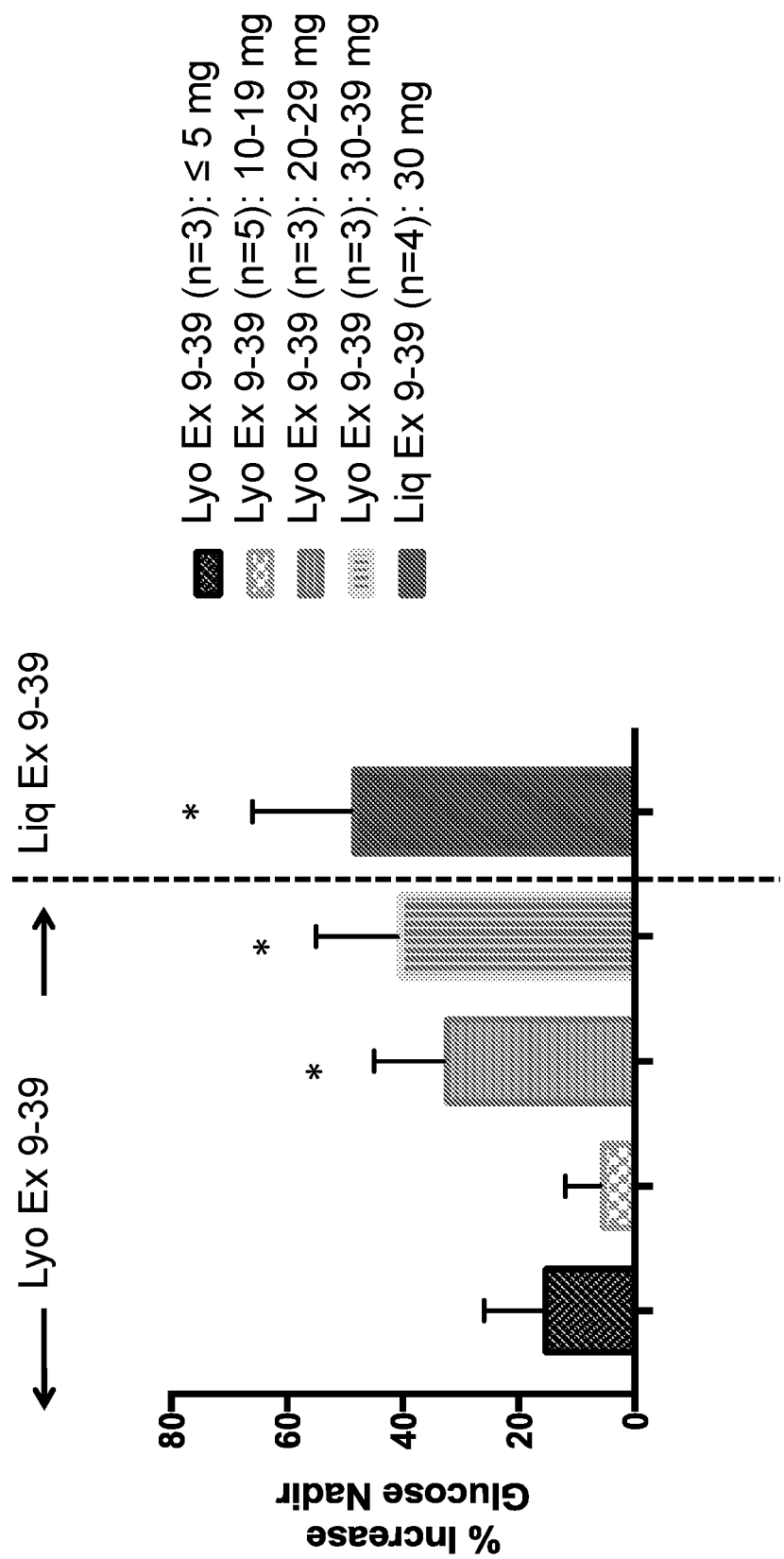

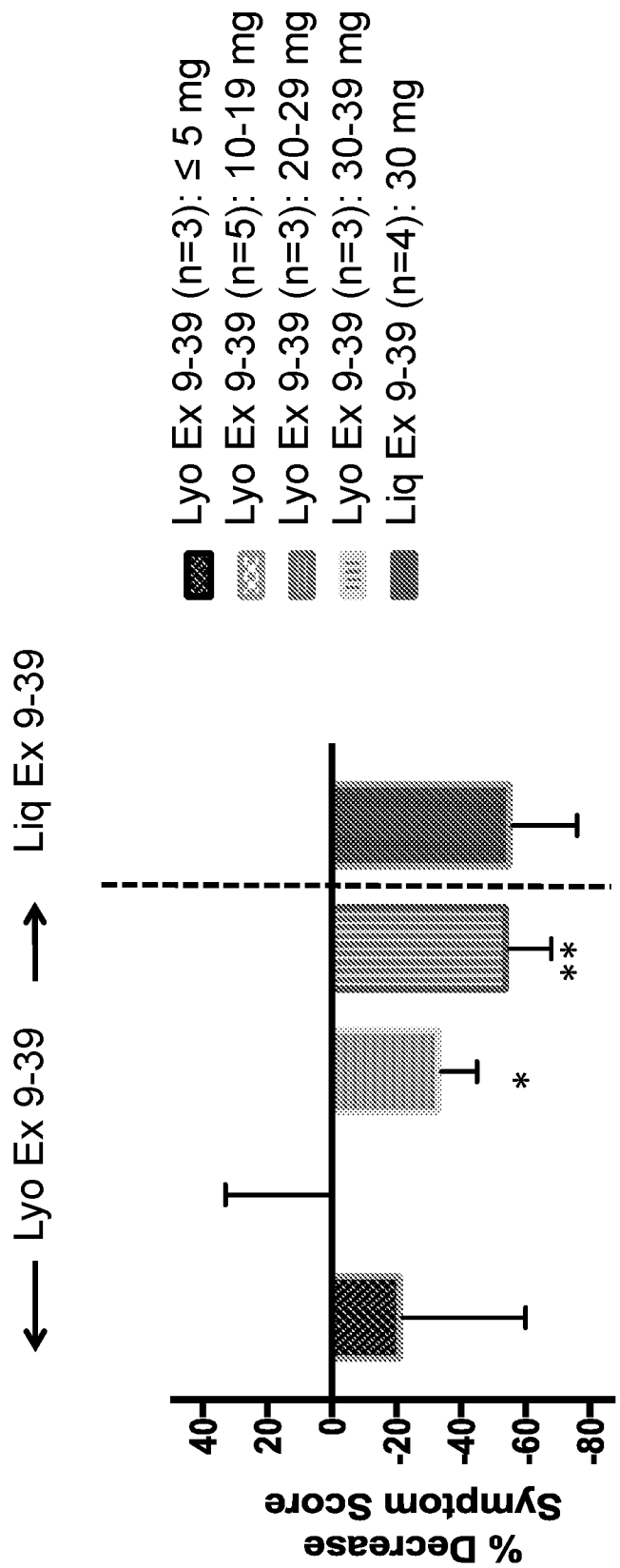

BUFFERED FORMULATIONS OF EXENDIN (9-39)

CROSS-REFERENCE TO RELATED APPLICATIONS

This application is a 371 National Stage entry of PCT Patent Application No. PCT/US2017/062838, filed Nov. 21, 2017, which claims the benefit of priority to U.S. Provisional Patent Application No. 62/424,979, filed Nov. 21, 2016, and to U.S. Provisional Patent Application No. 62/517,065, filed Jun. 8, 2017, the entire contents of each of which are incorporated by reference herein.

FIELD OF THE INVENTION

The present invention relates to improved pharmaceutical formulations of exendin (9-39) or a pharmaceutically acceptable salt thereof and a tonicity modifier in a physiologically acceptable buffer having a pH in the range of about 5 to about 6, and methods of using the formulations of exendin (9-39) for treating or preventing hyperinsulinemic hypoglycemia that includes post-bariatric hypoglycemia (PBH), and so relates to the fields of medicine, medicinal chemistry, pharmacology, chemistry, and biology.

BACKGROUND OF THE INVENTION

Insulin is a hormone secreted to control high blood glucose levels. Abnormal increases in insulin secretion can lead to profound hypoglycemia that can result in seizures, brain damage and death. Glucagon-like peptide-1 (GLP-1) is a gastrointestinal hormone that is released postprandially from intestinal L-cells and binds to GLP-1 receptors on beta cells of the pancreas, thereby enhancing insulin release. In patients with PBH, GLP-1-mediated insulin secretion is exaggerated.

Approximately 150,000-200,000 bariatric surgical procedures are performed in the United States each year. As the number of bariatric surgeries to treat severe obesity has increased, so too has the number of individuals who experience PBH. Accordingly, there is a growing unmet need for a therapy that safely and effectively mitigates hyperinsulinemic hypoglycemia and PBH.

Exendin (9-39) is a 31-amino acid peptide that selectively targets and blocks glucagon-like peptide-1 (GLP-1) receptors, normalizing insulin secretion by the pancreas in patients with PBH, thereby reducing hypoglycemia. Exendin (9-39) re-constituted in saline for intravenous or subcutaneous administration is currently undergoing human clinical trials as a treatment for PBH (Stanford Clinical Trials, Clinicaltrials.gov., clinical trials identifiers: NCT02771574 and NCT02550145). However, there remains a need for improved liquid pharmaceutical formulations of exendin (9-39) that provide improved potency, purity, and stability.

BRIEF SUMMARY OF THE INVENTION

In one aspect, liquid pharmaceutical formulations comprising exendin (9-39) or a pharmaceutically acceptable salt thereof in a physiological buffer having a pH in the range of about 5 to about 6 are provided. In some embodiments, the liquid pharmaceutical formulation comprises the pharmaceutically acceptable salt exendin (9-39) acetate or exendin (9-39) trifluoroacetate.

In some embodiments, the physiologically acceptable buffer is an acetate buffer, a citrate buffer, a phosphate buffer, or a histidine buffer. In some embodiments, the physiologically acceptable buffer is sodium acetate or sodium citrate. In some embodiments, the buffering agent (e.g., sodium acetate or sodium citrate) is present in the formulation at a concentration from about 5 mM to about 30 mM. In some embodiments, the buffering agent (e.g., sodium acetate or sodium citrate) is present in the formulation at a concentration from about 10 mM to about 30 mM (e.g., from 10 mM to 20 mM). In some embodiments, the physiologically acceptable buffer comprises sodium acetate at a concentration of about 10 mM, about 20 mM, or about 30 mM. In some embodiments, the physiologically acceptable buffer comprises sodium acetate at a concentration of about 10 mM. In some embodiments, the physiologically acceptable buffer comprises sodium citrate at a concentration of about 10 mM. In some embodiments, the physiologically acceptable buffer comprises sodium acetate at a concentration of at least 10 mM. In some embodiments, the physiologically acceptable buffer comprises sodium citrate at a concentration of at least 10 mM.

In some embodiments, the buffered liquid formulation comprises a tonicity modifier. In some embodiments, the tonicity modifier comprises mannitol, dextrose, glycerin, lactose, sucrose, trehalose, or a mixture thereof. In some embodiments, the tonicity modifier is mannitol. In some embodiments, the tonicity modifier is present at a concentration of about 20 to about 60 mg/ml. In some embodiments, the tonicity modifier is present at a concentration of about 45 mg/ml. In some embodiments, the tonicity modifier is present at a concentration of at least 20 mg/ml. In some embodiments, the tonicity modifier is added to target an isophysiological osmolality of about 290 mOsm/kg.

In some embodiments, the buffered liquid formulation has a pH above 5, e.g., at least pH 5.1 to about pH 6.0. In some embodiments, the buffered liquid formulation comprises a buffer having a pH in the range of 5.2 to 5.8. In some embodiments, the buffer has a pH of about 5.5.

In some embodiments, the buffered liquid formulation comprises exendin (9-39) or the pharmaceutically acceptable salt thereof at a concentration (e.g., peptide concentration) of about 10 to about 60 mg/ml (e.g., about 10 mg/ml, about 15 mg/ml, about 20 mg/ml, about 25 mg/ml, about 30 mg/ml, about 35 mg/ml, about 40 mg/ml, about 45 mg/ml, about 50 mg/ml, about 55 mg/ml, or about 60 mg/ml). In some embodiments, the buffered liquid formulation comprises exendin (9-39) or the pharmaceutically acceptable salt thereof at a concentration of about 30 to about 180 mg/ml, e.g., from about 30 mg/ml to about 150 mg/ml, from about 30 mg/ml to about 120 mg/ml, from about 50 mg/ml to about 150 mg/ml, or from about 60 mg/ml to about 120 mg/ml (e.g., about 30 mg/ml, about 40 mg/ml, about 50 mg/ml, about 60 mg/ml, about 70 mg/ml, about 80 mg/ml, about 90 mg/ml, about 100 mg/ml, about 110 mg/ml, about 120 mg/ml, about 130 mg/ml, about 140 mg/ml, about 150 mg/ml, about 160 mg/ml, about 170 mg/ml, or about 180 mg/ml). In some embodiments, the buffered liquid formulation comprises exendin (9-39) or the pharmaceutically acceptable salt thereof at a concentration of about 15 mg/ml, 30 mg/ml, 45 mg/ml, or 60 mg/ml. In some embodiments, the buffered liquid formulation comprises exendin (9-39) or the pharmaceutically acceptable salt thereof at a concentration of at least 15 mg/ml. In some embodiments, the buffered liquid formulation comprises exendin (9-39) or the pharmaceutically acceptable salt thereof at a concentration of about 30 mg/ml. In some embodiments, the buffered liquid formulation comprises exendin (9-39) or the pharmaceutically acceptable salt thereof at a concentration above 30 mg/ml. In some embodiments, the buffered liquid formulation comprises exendin (9-39) or the pharmaceutically acceptable salt thereof at a concentration of at least 60 mg/ml. In some embodiments, the buffered liquid formulation comprises exendin (9-39) or the pharmaceutically acceptable salt thereof at a concentration of about 60 mg/ml. In some embodiments, the buffered liquid formulation comprises exendin (9-39) or the pharmaceutically acceptable salt thereof at a concentration of about 90 mg/ml. In some embodiments, the buffered liquid formulation comprises exendin (9-39) or the pharmaceutically acceptable salt thereof at a concentration of about 120 mg/ml.

In some embodiments, the buffered liquid formulation comprising exendin (9-39) or the pharmaceutically acceptable salt thereof does not exhibit detectable aggregation of the exendin (9-39) or pharmaceutically acceptable salt thereof. In some embodiments, the buffered liquid formulation does not exhibit detectable aggregation of the exendin (9-39) or pharmaceutically acceptable salt thereof, as determined by whether the buffered liquid formulation remains as a non-gelatinous solution when stored at 50° C. for 18, 24, 36, 48 or 72 hours. In some embodiments, the buffered liquid formulation does not exhibit detectable aggregation of the exendin (9-39) or pharmaceutically acceptable salt thereof, as determined by visual or light microscopy inspection of the buffered liquid formulation for aggregation or precipitation when stored at 50° C. for 18, 24, 36, 48 or 72 hours.

In some embodiments, the buffered liquid formulation comprising exendin (9-39) or the pharmaceutically acceptable salt thereof as described herein is formulated for subcutaneous administration. In some embodiments, the buffered liquid formulation is formulated for once a day (QD) or twice a day (BID) subcutaneous administration. In some embodiments, the buffered liquid formulation is administered in the morning, in the evening, or both. In some embodiments, the buffered liquid formulation is administered QD by subcutaneous injection in the morning (e.g., at least 60 minutes before a morning meal).

In some embodiments, the buffered liquid formulation is administered BID by subcutaneous injection (e.g., in the morning and in the evening).

In some embodiments, a buffered liquid formulation comprising exendin (9-39) or a pharmaceutically acceptable salt thereof as described herein, when administered to a human subject, exhibits an improved pharmacokinetic profile as compared to a composition comprising the same dose of exendin (9-39) or a pharmaceutically acceptable salt thereof formulated in 0.9% normal saline. In some embodiments, the buffered liquid formulation exhibits a higher $C_{max}$ of exendin (9-39) (e.g., as measured in a plasma sample from a subject administered the formulation) than a composition comprising the same dose of exendin (9-39) or a pharmaceutically acceptable salt thereof formulated in 0.9% normal saline.

In another aspect, therapeutic methods using a buffered liquid exendin (9-39) formulation as described herein are provided. In some embodiments, methods of treating or preventing hyperinsulinemic hypoglycemia are provided. In some embodiments, methods of treating or preventing post-bariatric hypoglycemia are provided. In some embodiments, a buffered liquid exendin (9-39) formulation as described herein is administered to a subject twice daily (BID) at a dosage in the range of 5 mg-30 mg, e.g., about 7.5-30 mg BID or about 10-30 mg BID, e.g., at a dosage of about 7.5 mg, about 10 mg, about 15 mg, about 20 mg, about 25 mg, or about 30 mg BID. In some embodiments, a buffered liquid exendin (9-39) formulation as described herein is administered to a subject once daily (QD) at a dosage in the range of 20 mg-75 mg, e.g., about 30-75 mg QD, 30-60 mg QD, 40-70 mg QD, or 30-60 mg QD, e.g., at a dosage of about 30 mg, about 35 mg, about 40 mg, about 45 mg, about 50 mg, about 55 mg, about 60 mg, about 65 mg, about 70 mg, or about 75 mg QD. In some embodiments, a buffered liquid exendin (9-39) formulation as described herein is administered to a subject at a dosage of about 60 mg QD. In some embodiments, a buffered liquid exendin (9-39) formulation as described herein is administered to a subject at a dosage of about 30 mg BID. In some embodiments, methods of treating or preventing hyperinsulinemic hypoglycemia include administration of the buffered liquid exendin (9-39) formulation to a subject who has previously had an upper-gastrointestinal procedure, e.g., a bariatric or metabolic procedure (e.g., gastric bypass surgery).

BRIEF DESCRIPTION OF THE DRAWINGS

FIG. 3. Graphical representation of the effect of pH on purity and potency of a formulation having an exendin (9-39) concentration equivalent to 15 mg/ml, prepared in 10 mM sodium acetate, over a 5 day time course at 50° C.

FIG. 4. Graphical representation of the effect of pH on impurities observed in a formulation having an exendin (9-39) concentration equivalent to 15 mg/ml, prepared in 10 mM sodium acetate.

FIG. 7A-7D. Mean metabolic responses to OGTT at baseline and final day of treatment with ~30 mg lyophilized exendin (9-39) reconstituted in saline ("Lyo Ex 9-39") (A, C), n=6, or a 30 mg buffered liquid exendin (9-39) formulation ("Liq Ex 9-39") (B, D), n=4. Plasma concentrations (mean±SEM) versus time and inset AUC levels (mean±SEM) are shown for glucose (A,B) and insulin (C,D). Baseline (BL): solid line with circles, black bar (inset). Lyo Ex 9-39: dashed line with squares, red bar (inset). Liq Ex 9-39: dashed line with triangles, blue bar (inset). All baseline studies were stopped at glucose <50 mg/dL and IV dextrose was administered. Baseline data shown beyond 120 minutes represents the last observation carried forward (LOCF), thereby underestimating the true difference between treatment and baseline results. P-values by paired two-tailed paired Student's t tests: *≤0.05; **≤0.01.

FIG. 8A-8C. Improvements in response to OGTT between baseline and final day of treatment with multiple ascending doses of lyophilized exendin (9-39) reconstituted in saline ("Lyo Ex 9-39") (green, yellow, orange, red) and a 30 mg buffered liquid exendin (9-39) formulation ("Liq Ex 9-39") (blue). Percent change (mean±SEM) is shown for glucose nadir (A), insulin peak (B), and hypoglycemic symptom score (C). Symptoms graded on 5-point Likert scale (0=none; 5=severe) imposed on the Edinburgh Hypoglycemia Symptom Scale: autonomic (sweating, shaking, palpitations, hunger); neuroglycopenic (blurred vision, confusion, drowsiness, odd behavior, speech difficulty, incoordination, dizziness, inability to concentrate); malaise (nausea, headache). P-value by paired two-tailed paired Student's t tests: *≤0.05; **≤0.01. All baseline studies were stopped at glucose <50 mg/dL and IV dextrose was administered, thereby underestimating the percent improvement. Subjects receiving exendin (9-39) doses <18 mg required rescue with IV dextrose.

DETAILED DESCRIPTION OF THE INVENTION

I. Introduction

Figure 1:
FIG. 1. Light microscopy images showing aliquots of exendin (9-39) formulations prepared in 0.9% normal saline placed at 50° C. overnight. Left panel: aggregates formed after 24 hours and appeared gelatinous under microscope. Right panel: after 36 hours the solutions had a jelly-like sticky liquid appearance.

Exendin (9-39) is a glucagon-like peptide-1 (GLP-1) antagonist that selectively blocks GLP-1 receptors present on pancreatic cells, thereby preventing GLP-1-mediated enhancement of insulin secretion. Exendin (9-39) formulated in normal saline (0.9% sodium chloride, also referred to herein as "0.9% normal saline") has been administered in animal and human clinical studies for the treatment of hyperinsulinemic hypoglycemia. However, in the first clinical study involving subcutaneous injection of exendin (9-39) reconstituted in normal saline, an inverse dose-linearity was demonstrated with increasing concentration of injectate solution, suggesting concentration-dependent peptide aggregation and precipitation, with reduced pharmacokinetic exposure and clinical activity at higher concentrations. See, Example 3 of WO 2016/191395, incorporated by reference herein. Furthermore, as described herein in Examples 1 and 2, exendin (9-39) in normal saline has been shown to exhibit aggregation leading to lower exposure of exendin (9-39) under certain conditions, such as certain storage conditions or at certain concentrations of exendin (9-39).

Thus, in one aspect, the present disclosure provides for improved liquid pharmaceutical formulations of exendin (9-39) that exhibit reduced aggregation as compared to compositions comprising the same concentration of exendin (9-39) formulation in 0.9% normal saline. In another aspect, the present invention provides for formulations of exendin (9-39) that exhibit improved pharmacokinetic profiles as compared to a composition comprising the same dose of exendin (9-39) formulated in 0.9% normal saline. In some embodiments, for example as shown in Example 2, the buffered liquid exendin (9-39) formulations of the instant disclosure, when administered to a subject, exhibit a higher $C_{max}$ for exendin (9-39) than a composition comprising the same dose of exendin (9-39) or a pharmaceutically acceptable salt thereof formulated in 0.9% normal saline. Additionally, as described in Example 3, it has been found that the buffered liquid exendin (9-39) formulations of the instant disclosure confer greater pharmacokinetic exposure with longer duration of action as compared to exendin (9-39) formulated in 0.9% normal saline. Thus, the liquid pharmaceutical formulations of exendin (9-39) described herein also provide the advantage of improved pharmacokinetics. Additionally, the liquid pharmaceutical formulations of exendin (9-39) described herein can support lower and/or less frequent dosing for the treatment or prevention of hyperinsulinemic hypoglycemia.

II. Definitions

The terminology used herein is for the purpose of describing particular embodiments only, and is not intended to be limiting. Unless defined otherwise, all technical and scientific terms used herein have the same meaning as commonly understood by one of ordinary skill in the art to which this invention belongs. In this specification and in the claims that follow, reference will be made to a number of terms that shall be defined to have the following meanings unless a contrary intention is apparent. In some cases, terms with commonly understood meanings are defined herein for clarity and/or for ready reference, and the inclusion of such definitions herein should not be construed as representing a substantial difference over the definition of the term as generally understood in the art.

Although any methods and materials similar or equivalent to those described herein can be used in the practice or testing of the present invention, the preferred methods and materials are now described. All technical and patent publications cited herein are incorporated herein by reference in their entirety.

All numerical designations, e.g., pH, temperature, time, concentration, and molecular weight, including ranges, are approximations which are varied (+) or (−) by increments of 0.1 or 1.0, as appropriate (e.g., pH 5.4 or 5.5). It is to be understood, although not always explicitly stated, that all numerical designations are preceded by the term "about." References to ranges include the end-points unless indicated otherwise. For example, administration of a dose of exendin (9-39) in the range 15 mg/ml-45 mg/ml includes administration of 15 mg/ml or 45 mg/ml.

The singular forms "a," "an," and "the" include plural referents unless the context clearly dictates otherwise. Thus, for example, reference to "a compound" includes a plurality of compounds.

The term "comprising" is intended to mean that the compounds, compositions and methods include the recited elements, but not excluding others. "Consisting essentially of" when used to define compounds, compositions and methods, means excluding other elements that would materially affect the basic and novel characteristics of the claimed invention. "Consisting of" means excluding any element, step, or ingredient not specified in the claim. Embodiments defined by each of these transition terms are within the scope of this invention.

"Exendin (9-39)" or "Ex(9-39)" or "Ex9" refers to a 31 amino acid peptide with an empirical formula of $C_{149}H_{234}N_{40}O_{42}S$ and a molecular weight of 3369.8 Daltons. Exendin (9-39) comprises residues 9-39 of the GLP-1 receptor agonist exendin-4 and is a GLP-1 receptor antagonist. See, Montrose-Rafizadeh et al., *Journal of Biological Chemistry*, 272:21201-21206 (1997). The amino acid sequence for exendin (9-39) is shown as follows: H-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-$NH_2$ (SEQ ID NO: 1). Exendin (9-39) has a predicted isoelectric point of 4.69 and has a net charge of −1 at pH 6 that increases to a net charge of +4 at pH 3.0. As used herein, the term "exendin (9-39)" also encompasses pharmaceutically acceptable salts of exendin (9-39), including but not limited to sulfate, hydrochloride, phosophate, sulfamate, acetate, citrate, lactate, tartrate, methanesulfonate, ethanesulfonate, benzenesulfonate, p-toluenesulfonate, cyclohexylsulfamate and quinate salts. In some embodiments, exendin (9-39) is in the form of exendin (9-39) acetate or exendin (9-39) trifluoroacetate. Where not otherwise specified herein, exendin (9-39) acetate is used. Exendin (9-39) and pharmaceutically acceptable salts thereof are commercially available (e.g., Bachem (Clinalfa, Läufelfingen, Switzerland)).

As used herein, the term "tonicity modifier" refers to a compound or agent that adjusts the tonicity (osmotic pressure gradient) of a solution to prevent harmful effects that can occur upon administration of a solution that differs significantly from the tonicity of physiologic fluids. In some embodiments, a tonicity modifier comprises mannitol, dextrose, glycerin, lactose, sucrose, trehalose, or a mixture thereof.

As used herein, the term "physiologically acceptable buffer" refers to a solution that is suitable for use in a formulation for administration to a subject and that has the effect of maintaining or controlling the pH of the formulation in the pH range desired for the formulation. In some embodiments, the physiologically acceptable buffer maintains the pH of the formulation in a pH range of about 5 to about 6. In some embodiments, the physiologically acceptable buffer maintains the pH of the formulation at a pH above 5. Acceptable buffers include, but are not limited to, acetate buffers, citrate buffers, phosphate buffers, and mixtures thereof.

The term "pharmaceutical formulation" or "pharmaceutical formulation," as used herein, refers to a composition suitable for administration to a subject. Generally a pharmaceutical formulation is sterile, and preferably free of contaminants that are capable of eliciting an undesirable response within the subject (e.g., the compounds in the pharmaceutical formulation are pharmaceutical grade). Pharmaceutical formulations can be designed for administration to subjects or patients in need thereof via a number of different routes of administration, including oral, intravenous, buccal, rectal, parenteral, intraperitoneal, intradermal, intramuscular, subcutaneous, inhalational and the like. In some embodiments, a pharmaceutical formulation as described herein is formulated for subcutaneous administration.

As used herein, a "therapeutically effective amount" is an amount of an active ingredient (e.g., exendin (9-39) or its pharmaceutically acceptable salt) that eliminates, ameliorates, alleviates, or provides relief of the symptoms or clinical outcomes for which it is administered.

The terms "treatment," "treating," and "treat," as used herein in reference to administering exendin (9-39) to treat hyperinsulinemic hypoglycemia, covers any treatment of a disease in a human subject, and includes: (a) reducing the risk, frequency or severity of hypoglycemic episodes in patients with a history of hyperinsulinemic hypoglycemia, (b) reducing the risk of occurrence of hypoglycemia in a subject determined to be predisposed to the disease, such as a person who has received post-bariatric surgery, but not yet diagnosed as having the disease, (c) impeding the development of the disease; and/or (d) relieving the disease, i.e., causing regression of the disease and/or relieving one or more disease symptoms.

The terms "administer," "administering," and "administration" as used herein, refer to introducing a compound (e.g., exendin (9-39)), a composition, or an agent into a subject or patient, such as a human. As used herein, the terms encompass both direct administration, (e.g., self-administration or administration to a patient by a medical professional) and indirect administration (e.g., the act of prescribing a compound or composition to a subject).

"QD" and "BID" have their usual meanings of, respectively, administration of a buffered liquid formulation of exendin (9-39) once per day or twice per day. In some embodiments, administration once per day (QD) means that at least 20 hours, at least 22 hours, or about 24 hours elapse between administrations. In some embodiments, administration once per day means administration about every 24 hours. In some embodiments, administration twice per day (BID) means that at least 4 hours, at least 6 hours, at least 8 hours, at least 10 hours, at least 11 hours, or about 12 hours elapse between administrations. In some embodiments, administration twice per day means administration about every 12 hours.

As used herein, the terms "patient" and "subject" interchangeably refer to an individual (e.g., a human or a non-human mammal) having or prone to a condition that can be treated or prevented by administration of an exendin (9-39) formulation as provided herein. In some embodiments, a patient or subject has hyperinsulinemic hypoglycemia. In some embodiments, a patient or subject has previously had a bariatric procedure (e.g., gastric bypass surgery).

As used herein, the terms "aggregate," "aggregation," and "precipitation" are used interchangeably to refer to a physical interaction between exendin (9-39) polypeptides in a formulation that results in formation of oligomers, which may form large aggregates that can precipitate from solution. In some embodiments, large aggregates of exendin (9-39) may by visible to the naked eye or may be visible using detection methods known in the art, such as light microscopy. In some embodiments, aggregate formation by a polypeptide, such as during storage of a formulation, can adversely affect biological activity of the polypeptide, resulting in loss of therapeutic efficacy of the pharmaceutical formulation. In some embodiments, a formulation comprising exendin (9-39) as described herein does not exhibit "detectable aggregation," e.g., upon storage or administration to a subject, when aggregates are not visible by light microscopy (e.g., after a period of time such as 24, 36, or 48 hours).

The term "stored" or "storage" as used herein refers to storage of a formulation, e.g., a buffered liquid formulation comprising exendin (9-39) or a pharmaceutically acceptable salt thereof as described herein, at a specified temperature for a specified period of time. In some embodiments, the formulation is stored for a prolonged period of time (e.g., one month, two months, three months, four months, five months, six months or longer). In some embodiments, the formulation is stored at a temperature of about 5° C., 25° C., 30° C., 37° C., 40° C., or 50° C. In some embodiments, the formulation is stored at a defined temperature for a defined period of time (e.g., at 50° C.) for a defined period of time (e.g., 12 hours, 24 hours, 36 hours, 48 hours, 60 hours, or 72 hours) for the purposes of testing one or more properties of the formulation, e.g., for testing whether the formulation exhibits aggregation.

III. Exendin (9-39) Formulations

In one aspect, buffered liquid formulations are provided that comprise exendin (9-39) or a pharmaceutically acceptable salt thereof in a physiologically acceptable buffer having a pH above 5.0. In some embodiments, buffered liquid formulations are provided that comprise exendin (9-39) or a pharmaceutically acceptable salt thereof in a physiologically acceptable buffer having a pH in the range of about 5 to about 6. In some embodiments, the formulation further comprises a tonicity modifier.

As described herein, it has been surprisingly found that certain properties and pharmacokinetic parameters of a buffered liquid formulation comprising exendin (9-39) or the pharmaceutically acceptable salt thereof can be modulated by selecting an appropriate exendin (9-39) concentration, tonicity modifier, physiologically acceptable buffer, and pH. For example, as described in Example 1 below, buffered liquid formulations comprising exendin (9-39) or the pharmaceutically acceptable salt thereof can be improved with respect to properties such as exendin (9-39) aggregation after storage for period of time, potency of exendin (9-39) after storage for a period of time, and purity of exendin (9-39) after storage for a period of time by the selection of the exendin (9-39) concentration, tonicity modifier, physiologically acceptable buffer, and pH.

It has also been found, as described in Examples 2 and 3 below, that formulations comprising exendin (9-39) in a physiologically acceptable buffer having a pH above 5, e.g., a pH in the range of about 5 to about 6, exhibit improved pharmacokinetic properties relative to reconstituted lyophilized exendin (9-39) known in the art. For example, Example 2 shows that subcutaneous injection of a buffered exendin (9-39) formulation resulted in a higher $C_{max}$ for exendin (9-39) in plasma relative to a composition comprising the same dose of exendin (9-39) or a pharmaceutically acceptable salt thereof formulated in 0.9% normal saline. See, FIG. 5A and FIG. 5B. Example 3 shows that subcutaneous injection of a buffered exendin (9-39) formulation resulted in a higher $C_{max}$, a higher 12-hour AUC, and higher trough plasma concentrations of exendin (9-39) as compared to reconstituted lyophilized exendin (9-39).

Exendin (9-39)

In some embodiments, the buffered formulation comprises exendin (9-39). In some embodiments, the formulation comprises a pharmaceutically acceptable salt of exendin (9-39). In some embodiments, the formulation comprises the pharmaceutically acceptable salt exendin (9-39) acetate or exendin (9-39) trifluoroacetate.

In some embodiments, the formulation comprises exendin (9-39) or a pharmaceutically acceptable salt thereof at a concentration of about 4-90 mg/ml, about 4-60 mg/ml, about 4-45 mg/ml, about 10-90 mg/ml, about 10-60 mg/ml, about 10-45 mg/ml, about 10-40 mg/ml, about 10-35 mg/ml, about 10-30 mg/ml, about 12-25 mg/ml, about 12-20 mg/ml, about 12-15 mg/ml, about 30-90 mg/ml, about 30-60 mg/ml, about 30-70 mg/ml, about 45-90 mg/ml, about 45-75 mg/ml, about 60-90 mg/ml, or about 30-70 mg/ml (e.g., about 4 mg/ml, about 5 mg/ml, about 6 mg/ml, about 7 mg/ml, about 8 mg/ml, about 9 mg/ml, about 10 mg/ml, about 11 mg/ml, about 12 mg/ml, about 13 mg/ml, about 14 mg/ml, about 15 mg/ml, about 16 mg/ml, about 17 mg/ml, about 18 mg/ml, about 19 mg/ml, about 20 mg/ml, about 25 mg/ml, about 30 mg/ml, about 35 mg/ml, about 40 mg/ml, about 45 mg/ml, about 50 mg/ml, about 55 mg/ml, about 60 mg/ml, about 65 mg/ml, about 70 mg/ml, about 75 mg/ml, about 80 mg/ml, about 85 mg/ml, or about 90 mg/ml). In some embodiments, the formulation comprises exendin (9-39) at a concentration of about 15 mg/ml to about 45 mg/ml. In some embodiments, the formulation comprises exendin (9-39) at a concentration of about 15 mg/ml. In some embodiments, the formulation comprises exendin (9-39) at a concentration in the range of about 25 mg/ml to about 35 mg/ml. In some embodiments, the formulation comprises exendin (9-39) at a concentration of about 30 mg/ml. In some embodiments, the formulation comprises exendin (9-39) at a concentration in the range of about 40 mg/ml to about 50 mg/ml. In some embodiments, the formulation comprises exendin (9-39) at a concentration of about 45 mg/ml. In some embodiments, the formulation comprises exendin (9-39) at a concentration in the range of about 30 mg/ml to about 60 mg/ml. In some embodiments, the formulation comprises exendin (9-39) at a concentration in the range of about 30 mg/ml to about 90 mg/ml. In some embodiments, the formulation comprises exendin (9-39) at a concentration in the range of about 45 mg/ml to about 90 mg/ml. In some embodiments, the formulation comprises exendin (9-39) at a concentration of about 60 mg/ml. In some embodiments, the formulation comprises exendin (9-39) at a concentration of about 75 mg/ml.

Physiologically Acceptable Buffers

In some embodiments, the buffered liquid formulation comprises exendin (9-39) or the pharmaceutically acceptable salt thereof in a physiologically acceptable buffer having a pH in the range of about 5 to about 6. In some embodiments, the buffer is compatible with subcutaneous administration. In some embodiments, the physiologically acceptable buffer is a buffer that results in a liquid formulation having a pH at or about physiological pH, or within a relatively narrow pH range near physiological pH (e.g., between about 5.0 to about 8.0). In some embodiments, the physiologically acceptable buffer is at a pH that prevents, limits, or reduces the formation of exendin (9-39) aggregates in the liquid pharmaceutical formulation upon storage or administration to a subject. In some embodiments, the physiologically acceptable buffer has a pH above 5.0.

In one embodiment, a physiologically acceptable buffer comprises a solution having a stable pH over a prolonged period of time (e.g., about 1 hour, about 2 hours, about 4 hours, about 8 hours, about 12 hours, about 3 days, about 5 days, about 7 days, about 10 days, about 14 days, about 1 month, or longer). In one embodiment, a physiologically acceptable buffer comprises a solution that stabilizes the functionality of the exendin (9-39) during prolonged storage. In one embodiment, the storage can comprise about 1 hour, about 2 hours, about 4 hours, about 8 hours, about 12 hours, about 3 days, about 5 days, about 7 days, about 10 days, about 14 days, about 1 month, or longer.

In one embodiment, the buffered liquid formulation comprises a physiologically acceptable buffer having a pH in the range of about 5 to about 6 (e.g., a range including 5.0, 5.1, 5.2, 5.3, 5.4, 5.5, 5.6, 5.7, 5.8, 5.9 and 6.0). In one embodiment, the buffered liquid formulation comprises a physiologically acceptable buffer having a pH above 5.0 and up to about 6. In one embodiment, the physiologically acceptable buffer has a pH above 5.0 and up to about 5.5. In one embodiment, the physiologically acceptable buffer has a pH in the range of 5.2 to 5.8 (e.g., 5.2, 5.3, 5.4, 5.5, 5.6, 5.7, or 5.8). In one embodiment, the physiologically acceptable buffer has a pH in the range of 5.0 to 5.5 (e.g., 5.1, 5.2, 5.3, 5.4, or 5.5). In one embodiment, the physiologically acceptable buffer has a pH in the range of about 5.5 to about 6. In one embodiment, the physiologically acceptable buffer has a pH of about 5.5.

In one embodiment, the physiologically acceptable buffer comprises an acetate buffer, a citrate buffer, a phosphate buffer, a histidine buffer, or a mixture thereof. In one embodiment, the physiologically acceptable buffer comprises sodium acetate, potassium acetate, trisodium citrate, magnesium citrate, potassium citrate, potassium phosphate, or a mixture thereof. In one embodiment, the physiologically acceptable buffer comprises a buffering agent (e.g., sodium acetate) at a concentration from about 5 mM to about 30 mM, about 10 mM to about 30 mM, about 15 mM to about 30 mM, about 20 mM to about 30 mM, or about 25 mM to about 30 mM (e.g., about 5 mM, about 8 mM, about 10 mM, about 12 mM, about 15 mM, about 18 mM, about 20 mM, about 22 mM, about 25 mM, about 28 mM, or about 30 mM). In some embodiments, the physiologically acceptable buffer comprises the buffering agent (e.g., sodium acetate) at a concentration of at least 10 mM.

In some embodiments, the physiologically acceptable buffer comprises an acetate buffer. In some embodiments, the buffering agent is sodium acetate. In some embodiments, the buffering agent is potassium acetate. In some embodiments, the physiologically acceptable buffer comprises an acetate buffer (e.g., sodium acetate or potassium acetate) at a concentration of about 5 mM to about 30 mM, e.g., about 10 mM to about 20 mM. In some embodiments, the physiologically acceptable buffer comprises an acetate buffer (e.g., sodium acetate or potassium acetate) at a concentration of about 10 mM.

In some embodiments, the physiologically acceptable buffer comprises a citrate buffer. In some embodiments, the buffering agent is trisodium citrate. In some embodiments, the buffering agent is magnesium citrate. In some embodiments, the buffering agent is potassium citrate. In one embodiment, the physiologically acceptable buffer comprises the citrate buffer (e.g., sodium citrate, magnesium citrate, or potassium citrate) at a concentration from about 5 mM to about 30 mM, e.g., about 10 mM to about 20 mM. In some embodiments, the physiologically acceptable buffer comprises the citrate buffer (e.g., sodium citrate, magnesium citrate, or potassium citrate) at a concentration of about 10 mM.

In one embodiment, the physiologically acceptable buffer comprises a phosphate buffer. In one embodiment, the physiologically acceptable buffer comprises potassium phosphate. In one embodiment, the physiologically acceptable buffer comprises potassium phosphate at a concentration from about 5 mM to about 30 mM, e.g., about 10 mM to about 20 mM. In some embodiments, the physiologically acceptable buffer comprises the phosphate buffer (e.g., potassium phosphate) at a concentration of about 10 mM.

Tonicity Modifiers

In some embodiments, the buffered formulation comprises a tonicity modifier. In some embodiments, the tonicity modifier is mannitol, dextrose, glycerin, lactose, sucrose, trehalose, or a mixture thereof. In some embodiments, the tonicity modifier is mannitol. The use of tonicity modifiers is well known in the medicinal arts, and one of skill in the art can use one or more of the tonicity modifiers disclosed herein to provide a liquid pharmaceutical formulation suitable for subcutaneous administration. See, for example, Pramanick et al., *Pharma Times*, Vol 45, No. 3, (2013); see also, *Formulating Poorly Water Soluble Drugs*, Williams, Watts, and Miller, eds., Springer Science and Business Media (2011).

In some embodiments, the tonicity modifier or combination of tonicity modifiers is present in the formulation at a concentration of about 20-75 mg/ml, about 20-60 mg/ml, about 25-55 mg/ml, about 30-75 mg/ml, about 30-50 mg/ml, about 35-45 mg/ml, about 40-45 mg/ml, about 45-75 mg/ml, or about 45-60 mg/ml (e.g., about 20 mg/ml, about 22 mg/ml, about 25 mg/ml, about 28 mg/ml, about 30 mg/ml, about 32 mg/ml, about 35 mg/ml, about 38 mg/ml, about 40 mg/ml, about 42 mg/ml, about 45 mg/ml, about 48 mg/ml, about 50 mg/ml, about 52 mg/ml, about 55 mg/ml, about 58 mg/ml, about 60 mg/ml, about 65 mg/ml, about 70 mg/ml, or about 75 mg/ml). In some embodiments, the formulation comprises the tonicity modifier at a concentration range of about 30 mg/ml to about 60 mg/ml.

In some embodiments, the tonicity modifier or combination of tonicity modifiers is present in the formulation in an amount that results in the formulation having an isophysiological osmolality. In some embodiments, the tonicity modifier or combination of tonicity modifiers is present in the formulation in an amount that results in the formulation having an osmolality of about 275 to 300 mOsm/kg (e.g., about 275 mOsm/kg, about 280 mOsm/kg, about 285 mOsm/kg, about 290 mOsm/kg, about 295 mOsm/kg, or about 300 mOsm/kg). In some embodiments, the tonicity modifier or combination of tonicity modifiers (e.g., mannitol, dextrose, glycerin, lactose, sucrose, trehalose, or a combination thereof) is present in the formulation in an amount that results in the formulation having an osmolality of about 290 mOsm/kg.

In some embodiments, the tonicity modifier comprises mannitol. In some embodiments, the mannitol is present at a concentration of about 40-50 mg/ml. In some embodiments, the mannitol is present at a concentration in the range of about 40 mg/ml to about 45 mg/ml. In some embodiments, the mannitol is present at a concentration of about 45 mg/ml. In some embodiments, the mannitol is present at a concentration of at least 45 mg/ml.

In one embodiment, the tonicity modifier comprises dextrose. In one embodiment, the dextrose is present at a concentration of about 20 mg/ml to about 60 mg/ml (e.g., about 20 mg/ml, about 40 mg/ml, about 45 mg/ml, or about 60 mg/ml).

In one embodiment, the tonicity modifier comprises glycerin. In some embodiments, the glycerin is present at a concentration of about 20 mg/ml to about 60 mg/ml (e.g., about 20 mg/ml, about 40 mg/ml, about 45 mg/ml, or about 60 mg/ml).

In one embodiment, the tonicity modifier comprises lactose. In one aspect, the lactose is present at a concentration of about 20 mg/ml to about 60 mg/ml (e.g., about 20 mg/ml, about 40 mg/ml, about 45 mg/ml, or about 60 mg/ml).

In one embodiment, the tonicity modifier comprises sucrose. In some embodiments, the sucrose is present at a concentration of about 20 mg/ml to about 60 mg/ml (e.g., about 20 mg/ml, about 40 mg/ml, about 45 mg/ml, or about 60 mg/ml).

In one embodiment, the tonicity modifier comprises trehalose. In one aspect, the trehalose is present at a concentration of about 20 mg/ml to about 60 mg/ml (e.g., about 20 mg/ml, about 40 mg/ml, about 45 mg/ml, or about 60 mg/ml).

In some embodiments, the buffered formulation comprises two or more tonicity modifiers. In some embodiments, the buffered formulation comprises two or more tonicity modifiers selected from the group consisting of mannitol, dextrose, glycerin, lactose, sucrose, and trehalose. In some embodiments, the buffered formulation comprises mannitol at least one other tonicity modifier.

Additional Excipients

In some embodiments, the formulation further comprises one or more additional excipients such as preservatives, surfactants (e.g., a polysorbate or a poloxamer), or colorants (e.g., pharmaceutically acceptable dyes, inorganic pigments, and natural colorants). A wide variety of pharmaceutically acceptable excipients are known in the art. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., 7th ed., Lippincott, Williams, & Wilkins; and Handbook of Pharmaceutical Excipients (2000) A. H. Kibbe et al., eds., 3rd ed. Amer. Pharmaceutical Assoc., each of which is incorporated by reference herein.

IV. Therapeutic Methods

In another aspect, methods of treatment comprising administering a buffered liquid formulation comprising exendin (9-39) or a pharmaceutically acceptable salt thereof as described herein are provided. In some embodiments, the method comprises administering a buffered liquid formulation of exendin (9-39) as described herein in an amount effective to prevent or reduce the symptoms of hyperinsulinemic hypoglycemia. In some embodiments, the method comprises administering a buffered liquid formulation of exendin (9-39) as described herein in an amount effective to prevent or reduce the symptoms, metabolic outcomes, and/or clinical outcomes of post-bariatric hypoglycemia.

Patient Population

In some embodiments, a subject to be treated according to the methods described herein is a subject having hyperinsulinemic hypoglycemia (HH). In certain embodiments, the subject having hyperinsulinemic hypoglycemia has previously had bariatric surgery (e.g., Roux-en-Y Gastric Bypass) and/or a related metabolic procedure. In certain embodiments, the subject has previously had bariatric surgery (e.g., Roux-en-Y Gastric Bypass) and/or a related metabolic procedure and is at risk for developing hyperinsulinemic hypoglycemia. In some embodiments, the subject having hyperinsulinemic hypoglycemia has previously had an upper-gastrointestinal procedure, such as gastrectomy or esophagectomy.

"Hyperinsulinemic hypoglycemia," as used herein, encompasses the conditions dumping syndrome, late dumping syndrome, nesideoblastosis, noninsulinoma pancreatogenous hypoglycemia syndrome (NIPHS), and/or post-prandial reactive hypoglycemia. Hyperinsulinemic hypoglycemia may result from a gastric, bariatric, or metabolic procedure, such as a Roux-en-Y gastric bypass (RYGB) or vertical sleeve gastrectomy (VSG), or may have a congenital, acquired, or induced origin.

Subjects with hyperinsulinemic hypoglycemia may be identified by any suitable method. In some embodiments, hyperinsulinemic hypoglycemia is diagnosed by the presence of Whipple's triad, which has the following criteria: (1) the occurrence of hypoglycemic symptoms; (2) documented low plasma glucose level at the type of the symptoms; and (3) resolution of the symptoms after plasma glucose is raised. In some embodiments, hyperinsulinemic hypoglycemia is defined by the occurrence of capillary glucose 50 mg/dL at least once per month by report by the subject or medical record. In some embodiments, hyperinsulinemic hypoglycemia is defined by a plasma glucose concentration of <54 mg/dL detected by self-monitoring of plasma glucose, continuous glucose monitoring for at least 20 minutes, or a laboratory measurement of plasma glucose. In some embodiments, hyperinsulinemic hypoglycemia is defined by a plasma glucose concentration of 55 mg/dL during an oral glucose tolerance test or meal tolerance test in association with inappropriately elevated plasma insulin (≥3 uU/mL) or c-peptide (0.3 mg/dL) when glucose was 55 mg/dL. In some embodiments, hyperinsulinemic hypoglycemia is defined by a plasma glucose concentration of 60 mg/dL during an oral glucose tolerance test or meal tolerance test in association with inappropriately elevated plasma insulin (≥3 uU/mL) or c-peptide (>0.3 mg/dL) when glucose was ≤60 mg/dL. In some embodiments, hyperinsulinemic hypoglycemia is diagnosed by a positive provocative test, e.g., an oral glucose tolerance test (OGTT) or a mixed meal tolerance test (MMTT). See, Eisenberg et al., *Surgery for Obesity and Related Diseases*, 2017, 13:371-378; see also, *Diabetes Care*, 2016, doi: 10.2337/dc16-2215.

In one embodiment, the subject to be treated has previously had a bariatric procedure and/or related metabolic procedure, such as a Roux-en-Y Gastric Bypass procedure. Bariatric and/or related metabolic procedures include, but are not limited to, Roux-en-Y Gastric Bypass, Vertical Sleeve Gastrectomy, placement of an endosleeve device, such as the EndoBarrier Gastrointestinal Liner System, also called an "endoluminal liner," duodenal mucosal resurfacing, also referred to as duodenal ablation, partial bypass of the duodenum, involving duodeno-ileal or duodeno-jejunal anastomosis, vagal nerve blockade, and/or pyloroplasty).

A bariatric procedure (i.e., bariatric surgery) typically involves any of the foregoing: partially or completely bypassing the duodenum and/or decreasing nutrient exposure to the duodenum, increasing the rapidity of nutrient transit to the lower part of the intestines (often specifically the ileum), and/or otherwise increasing ileal nutrient exposure. Bariatric surgery may be intended for weight loss or metabolic benefit (such as resolution of diabetes), or both. Such weight loss or metabolic procedures, referred to herein as "bariatric procedures" may enhance secretion of GLP-1 from the distal small intestine, especially the ileum, leading to elevated insulin secretion, and in some subjects hypoglycemia. In some embodiments, the subject may be referred to as a "post bariatric surgery" subject or "post-RYGB."

In another embodiment, the subject to be treated has previously had a related metabolic procedure. As but one example, in one embodiment, the subject to be treated has previously had a non-bariatric surgical procedure involving the gastrointestinal system (including but not limited to esophagectomy, for example for treatment of esophageal cancer, Nissen Fundoplication, for example for treatment of gastroesophageal reflux, or gastrectomy, for example for treatment or prevention of gastric cancer) and so may be referred to herein as "post gastrointestinal surgery."

In another embodiment, the subject to be treated is prediabetic and/or insulin resistant and may benefit from prevention of pancreatic hyperstimulation from oral carbohydrate ingestion leading to post-prandial hypoglycemia. In another embodiment, the subject to be treated has a congenital, acquired, or induced form of hyperinsulinemic hypoglycemia, such as congenital hyperinsulinism or sometimes referred to as congenital nesidioblastosis.

Suitable patient populations and methods of identifying patients are also described in PCT Patent Application No. PCT/US2016/033837, incorporated by reference herein.

In some embodiments, the patient is a human patient. In some embodiments, the patient is an adult. In some embodiments, the patient is a juvenile. In some embodiments, the patient is an adult who has previously undergone a bariatric procedure (e.g., gastric bypass surgery).

Routes of Administration and Dosing Regimens

In some embodiments, a buffered liquid formulation comprising exendin (9-39) as described herein is administered by subcutaneous administration (e.g., subcutaneous injection). Sites of injection, include, but are not limited to, injection in the thigh, abdomen, upper arm region, or upper buttock region.

In some embodiments, buffered liquid exendin (9-39) formulations of the present disclosure are formulated for subcutaneous administration. In one embodiment, the buffered liquid exendin (9-39) formulations of the present invention are formulated for subcutaneous administration according to a once daily (QD) or twice daily (BID) regime.

Injectate Formulations

In some embodiments, the buffered liquid exendin (9-39) formulation is formulated as a single-use prefilled syringe, e.g., in a kit comprising multiple single-use prefilled syringes (e.g., 10, 20, 30, 40, 50, or 60 prefilled syringes). In some embodiments, the single-use prefilled syringe comprises an exendin (9-39) liquid pharmaceutical formulation comprising about 5-75 mg of exendin (9-39), a tonicity modifier, and a buffer having a pH in the range of 5.0 to 6.0.

In some embodiments, the buffered liquid exendin (9-39) formulation is formulated as a sterile, preserved isotonic solution in a unit or multi-dose glass vial or ampule for administration with the use of a syringe, similar to a glucagon emergency kit. In some embodiments, the buffered liquid exendin (9-39) formulation is provided as an injectable solution in a single-dose tray containing a vial of a buffered liquid exendin (9-39) formulation as described herein (e.g., a formulation comprising about 5-75 mg of exendin (9-39), a tonicity modifier, and a buffer having a pH of about 5.5, and optionally an appropriate volume of an antimicrobial preservative), a vial connector, a syringe, and one or more needles.

In some embodiments, the buffered liquid exendin (9-39) formulation is formulated as a sterile, preserved isotonic solution in a glass cartridge pen-injector device. As a non-limiting example, the formulation comprises about 5-75 mg of exendin (9-39) (e.g., about 5-45 mg or about 30-75 mg of exendin (9-39)), a tonicity modifier and a buffer having a pH in the range of about 5.5, and optionally an appropriate volume of an antimicrobial preservative.

In some embodiments, each dose is administered in a total volume ranging from 0.25-2 ml injectate, with most subjects administering an injection volume ranging from 0.5-1.5 ml, e.g., 0.7-1 ml.

Treatment Parameters

In some embodiments, compositions comprising a therapeutically effective dose of a liquid pharmaceutical formulation comprising exendin (9-39) or a pharmaceutically acceptable salt thereof and a tonicity modifier in a physiologically acceptable buffer having a pH in the range of about 5 to about 6 are administered to a subject in need thereof for the treatment or prevention of hyperinsulinemic hypoglycemia.

In one embodiment, the method comprises administering (e.g., subcutaneously administering) a therapeutically effective dose of exendin (9-39) or a pharmaceutically acceptable salt thereof and a tonicity modifier in a physiologically acceptable buffer having a pH in the range of about 5 to about 6 to a subject in need thereof. In some embodiments, the therapeutically effective amount of exendin (9-39) (or a pharmaceutically acceptable salt thereof) is an amount ranging from about 15 mg/ml to about 180 mg/ml, e.g., from about 15 mg/ml to about 60 mg/ml, from about 18 mg/ml to about 50 mg/ml, from about 20 mg/ml to about 30 mg/ml, from about 30 mg/ml to about 60 mg/ml, from about 30 mg/ml to about 45 mg/ml, from about 45 mg/ml to about 90 mg/ml, from about 45 mg/ml to about 60 mg/ml, from about 30 mg/ml to about 180 mg/ml, from about 30 mg/ml to about 150 mg/ml, from about 30 mg/ml to about 90 mg/ml, from about 30 mg/ml to about 120 mg/ml, from about 45 mg/ml to about 150 mg/ml, or from about 60 mg/ml to about 180 mg/ml. In some embodiments, the therapeutically effective amount of exendin (9-39) (or a pharmaceutically acceptable salt thereof) is an amount of about 15 mg/ml, about 18 mg/ml, about 20 mg/ml, about 25 mg/ml, about 30 mg/ml, about 35 mg/ml, about 40 mg/ml, about 42 mg/ml, about 45 mg/ml, about 48 mg/ml, about 50 mg/ml, about 52 mg/ml, about 55 mg/ml, about 58 mg/ml, about 60 mg/ml, about 65 mg/ml, about 70 mg/ml, about 75 mg/ml, about 80 mg/ml, about 85 mg/ml, or about 90 mg/ml.

In some embodiments, the method comprises administering (e.g., subcutaneously administering) a buffered liquid formulation of exendin (9-39) as described herein at a total daily dosage of exendin (9-39) from about 10 mg to about 90 mg, e.g., a total daily dosage of exendin (9-39) of about 10 mg to about 75 mg, about 10 mg to about 60 mg, about 15 mg to about 90 mg, about 15 mg to about 75 mg, about 15 mg to about 60 mg, about 20 mg to about 90 mg, about 20 mg to about 75 mg, about 25 mg to about 75 mg, about 25 mg to about 60 mg, about 30 mg to about 90 mg, about 30 mg to about 75 mg, about 30 mg to about 60 mg, or about 40 mg to about 90 mg. In some embodiments, the buffered formulation is administered at a total daily dosage of exendin (9-39) of at least about 20 mg, at least about 30 mg, at least about 40 mg, at least about 50 mg, or at least about 60 mg. In some embodiments, the buffered formulation is administered at a total daily dosage of exendin (9-39) of about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, or about 90 mg.

The dosage ranges described above are exemplary adult doses, and may vary depending upon the age and weight of the patient as would be known by those skilled in the pharmaceutical arts. It will be appreciated that in some embodiments, dosage may be increased or decreased during the course of treatment. For example, some physicians may desire to treat with a low or initiating (starting) dose, escalate to an increased dose if the initiating dose does not provide sufficient therapeutic benefit, and maintain the initiating dose if the initiating dose provides sufficient therapeutic benefit.

In some embodiments, a therapeutically effective amount of exendin (9-39) (or a pharmaceutically acceptable salt thereof) as a buffered liquid formulation is administered once daily (QD). QD administration is well-known in the medical arts. In some embodiments QD doses are administered (e.g., self-administered) at about 24 hour intervals (e.g., 7 a.m. on successive days). However, shorter (e.g., 8 a.m. and 6 a.m. on successive days) or longer (e.g., 7 a.m. and 9 a.m. on successive days) intervals between administration are possible provided the administrations are at least about 18 hours apart. Preferably, the administrations are at least about 20 hours, 21 hours, 22 hours, 23 hours, or 24 hours apart. Preferably, the administrations are not more than 30 hours apart. Although administration once a day is preferred, the dosage administered can occur more frequently (e.g., two times a day) or less frequently (e.g., once every other day).

In some embodiments, the buffered liquid formulation is administered twice daily (BID). BID (twice per day) administration is well known in the medical arts. The buffered liquid formulation can be administered at specific points in the day or schedule of a subject, e.g., morning, afternoon, evening, night, before or during or after meals, before bedtime, etc. In some embodiments, the liquid pharmaceutical formulation is administered about once every 12 hours. In some embodiments BID doses are administered (e.g., self-administered) at about 12 hour intervals (e.g., 7 a.m. and 7 p.m.). However, shorter (e.g., 8 a.m. and 6 p.m.) or longer (e.g., 7 a.m. and 10 p.m.) intervals between administrations are possible. In some embodiments, the administrations are at least about 4 hours, 6 hours, 7 hours, 8 hours, 9 hours, 10 hours or 11 hours apart. Preferably the administrations are not more than about 15 hours apart. Methods of timing the administration of BID dosing are described, for example, in PCT Patent Application No. PCT/US2016/033837, incorporated by reference herein.

In some embodiments, the buffered liquid formulation is administered (e.g., subcutaneously administered) at a dosage of exendin (9-39) in the range of 5 mg-30 mg BID or 10 mg-45 mg BID, e.g., about 7.5-30 mg BID, about 10-30 mg BID, about 15-45 mg BID, about 25-45 mg BID, or about 30-45 mg BID. In some embodiments, the buffered liquid formulation is administered at a dosage of about 7.5 mg BID. In some embodiments, the buffered liquid formulation is administered at a dosage of about 10 mg BID. In some embodiments, the buffered liquid formulation is administered at a dosage of about 15 mg BID. In some embodiments, the buffered liquid formulation is administered at a dosage of about 20 mg BID. In some embodiments, the buffered liquid formulation is administered at a dosage of about 30 mg BID. In some embodiments, the buffered liquid formulation is administered at a dosage of about 45 mg BID. In some embodiments, a buffered liquid formulation comprising exendin (9-39) at a concentration of 30 mg/ml or higher is administered at a dosage of about 30-45 mg BID, e.g., at a dosage of about 30 mg BID.

In some embodiments, the buffered liquid formulation is administered (e.g., subcutaneously administered) at a dosage of exendin (9-39) in the range of 20 mg-90 mg QD, e.g., about 30-90 mg QD, about 30-75 mg QD, about 45-90 mg QD, or about 45-75 mg QD. In some embodiments, the buffered liquid formulation is administered at a dosage of about 20 mg QD. In some embodiments, the buffered liquid formulation is administered at a dosage of about 30 mg QD. In some embodiments, the buffered liquid formulation is administered at a dosage of about 45 mg QD. In some embodiments, the buffered liquid formulation is administered at a dosage of about 60 mg QD. In some embodiments, the buffered liquid formulation is administered at a dosage of about 75 mg QD. In some embodiments, the buffered liquid formulation is administered at a dosage of about 90 mg QD. In some embodiments, a buffered liquid formulation comprising exendin (9-39) at a concentration of 60 mg/ml or higher is administered at a dosage of at least 45 mg QD, e.g., at a dosage of 45-90 mg QD, at a dosage of about 60 mg QD, or at a dosage of about 75 mg QD.

In some embodiments, the buffered liquid formulation is administered (e.g., subcutaneously administered) twice daily (BID) within about 60 minutes prior to morning and evening meals (or prior to the two main meals of the day). In some embodiments, the administrations prior to the morning and evening meals (or prior to the two main meals of the day) are at least about 6 hours apart. In some embodiments, the administration of the buffered liquid formulation is not timed to meals.

In some embodiments, the buffered liquid formulation is administered (e.g., subcutaneously administered) once daily (QD) in the morning or at night to maximally cover the morning and evening meals. For example, in some embodiments, the formulation is administered at night after the evening meal or early in the morning prior to the morning meal (e.g., at least 60 minutes prior to the morning meal).

In some embodiments, the buffered liquid formulation is administered (e.g., subcutaneously administered) twice daily (BID) at different doses. In some embodiments, the formulation is administered in the morning and in the afternoon at different doses. In some embodiments, the formulation is administered in the morning and in the evening or at night at different doses. For example, in some embodiments, the formulation is administered in the morning and in the evening or at night, wherein the evening or night dose is a lower dose than the morning dose.

Subjects who are administered a buffered liquid formulation comprising exendin (9-39) as described herein may receive therapy for a predetermined time, an indefinite time, or until an endpoint is reached. Treatment may be continued on a continuous daily or weekly basis for at least two to three months, six months, one year, or longer. In some embodiments, therapy is for at least 30 days, at least 60 days, at least 90 days, at least 120 days, at least 150 days, or at least 180 days. In some embodiments, treatment is continued for at least 6 months, at least 7 months, at least 8 months, at least 9 months, at least 10 months, at least 11 months, or at least one year. In some embodiments, treatment is continued for the rest of the patient's life or until administration is no longer effective to provide meaningful therapeutic benefit.

Improved Pharmacokinetic Properties

In some embodiments, a buffered liquid formulation comprising exendin (9-39) or a pharmaceutically acceptable salt thereof and a tonicity modifier in a physiologically acceptable buffer having a pH in the range of about 5 to about 6 results in an improved absorption profile of exendin (9-39) relative to a composition comprising the same dose of exendin (9-39) or a pharmaceutically acceptable salt thereof formulated in 0.9% normal saline. In some embodiments, the buffered liquid formulation results in a higher plasma concentration of exendin (9-39) over a period about 1-6 hours (e.g., over 1-4 hours, after about 1 hour, after about 2 hours, after about 3 hours, or after about 4 hours) after administration to a subject relative to the plasma concentration of exendin (9-39) over or at the same period of time of a subject administered the same dose of exendin (9-39) formulated in 0.9% normal saline.

In one embodiment, the buffered liquid exendin (9-39) formulation of the present disclosure, when administered to a subject, results in a greater increase in plasma concentrations of exendin (9-39) over a period of about 1 to 12 hours (e.g., over 1-10 hours, over 6-12 hours, over 1-8 hours, or over 4-12 hours, after about 1 hour, after about 2 hours, after about 3 hours, or after about 4 hours) after administration to a subject, as compared to the increase in plasma concentration over the same period of time of a subject administered a composition comprising the same dose of exendin (9-39) formulated in 0.9% normal saline solution. In some embodiments, the change in plasma concentration of exendin (9-39) is measured about 1 hour, 2 hours, 3 hours, 4 hours, 5 hours, or 6 hours after the exendin (9-39) formulation is administered to the subject.

In some embodiments, subcutaneous injection of a buffered liquid formulation comprising exendin (9-39) as described herein results in a higher $C_{max}$ of exendin (9-39) relative to a composition comprising the same dose of exendin (9-39) formulated in 0.9% normal saline.

In some embodiments, subcutaneous injection of a buffered liquid formulation comprising exendin (9-39) as described herein results in a higher AUC of exendin (9-39) relative to a composition comprising the same dose of exendin (9-39) formulated in 0.9% normal saline. For example, in some embodiments, subcutaneous injection of a buffered liquid formulation comprising exendin (9-39) as described herein results in a higher 12-hour AUC of exendin (9-39) relative to a composition comprising the same dose of exendin (9-39) formulated in 0.9% normal saline.

In some embodiments, subcutaneous injection of a buffered liquid formulation comprising exendin (9-39) as described herein results in a later $T_{max}$ for exendin (9-39) relative to a composition comprising the same dose of exendin (9-39) formulated in 0.9% normal saline.

In some embodiments, subcutaneous injection of a buffered liquid formulation comprising exendin (9-39) as described herein results in a higher trough concentration of exendin (9-39) relative to a composition comprising the same dose of exendin (9-39) formulated in 0.9% normal saline (e.g., when measured after repeat dosing, such as dosing for at least 3 days, dosing for at least 1 week, dosing for at least 2 weeks, or dosing for at least 1 month).

V. Examples

The following examples are provided to illustrate, but not to limit, the claimed invention.

Example 1: Properties of Reconstituted Exendin (9-39) in 0.9% Normal Saline and Buffered Exendin (9-39) Formulations This example describes physical and chemical properties of lyophilized exendin (9-39) acetate reconstituted in 0.9% normal saline as compared to the properties of buffered formulations of exendin (9-39).

Properties of Exendin (9-39) Formulated in Normal Saline

Different concentrations (5, 10.24, 15.3, 25.22, and 44.99 mg/ml) of lyophilized exendin (9-39) acetate were prepared by reconstituting in 0.9% normal saline and stored at 5° C. The pH of each reconstituted exendin (9-39) formulation was recorded at day zero and monitored for up to 14 days. All concentrations of the reconstituted exendin (9-39) formulations resulted in an initial pH of 4.4 to 4.5. A visual inspection of each reconstituted exendin (9-39) formulation was also noted on day zero and monitored for up to 14 days, while being held at 5° C. The results are shown in Table 1 below. No aggregation, gelling or precipitation of reconstituted exendin (9-39) formulations was observed in any of the samples held at 5° C. over the 14 day period.

TABLE 1

| Exendin 9-39 (mg/mL) | pH at T0 | Initial (T0) | Day 3, 4, 7, and 14 (5° C.) |
|---|---|---|---|
| 5.00 | 4.54 | Clear, particle free solution | Clear, particle free solution |
| 10.24 | 4.49 | Clear, particle free solution | Clear, particle free solution |
| 15.30 | 4.45 | Clear, particle free solution | Clear, particle free solution |
| 25.22 | 4.43 | Clear, particle free solution | Clear, particle free solution |
| 44.99 | 4.43 | Clear, particle free solution | Clear, particle free solution |

Aliquots of each of the reconstituted exendin (9-39) formulations (5, 10.24, 15.3, 25.22, and 44.99 mg/ml) held at 5° C. for seven days were placed at 50° C. overnight. All of the reconstituted exendin (9-39) formulations showed aggregation within 24 hrs at 50° C. and the aggregates appeared gelatinous under light microscopy (FIG. 1, left panel). After 36 hours at 50° C., the reconstituted exendin (9-39) formulations had further aggregated (FIG. 1, right panel).

To investigate further the temperature at which the reconstituted exendin (9-39) formulations in 0.9% saline began to precipitate and/or aggregate, aliquots of the 15 mg/ml reconstituted exendin (9-39) formulations were stored overnight at 5° C., 25° C., 30° C., 37° C., and 40° C. As shown in Table 2 below, a visual inspection of the reconstituted exendin (9-39) formulations demonstrated that none of the 15 mg/ml reconstituted exendin (9-39) formulations stored overnight up to 40° C. precipitated out of solution.

TABLE 2

| Storage Temp. | Exendin 9-39 (mg/mL) | Initial (T0) | Overnight |
|---|---|---|---|
| 5° C. | 15 | Clear, particle free solution | Clear, particle free solution |
| 25° C. | 15 | Clear, particle free solution | Clear, particle free solution |
| 30° C. | 15 | Clear, particle free solution | Clear, particle free solution |
| 37° C. | 15 | Clear, particle free solution | Clear, particle free solution |
| 40° C. | 15 | Clear, particle free solution | Clear, particle free solution |

Properties of Buffered Liquid Formulations of Exendin (9-39)

Exendin (9-39) acetate was formulated in one of two ionic buffers (an acetate buffer or a citrate buffer) of various ionic strengths (10 mM to 30 mM) and at different pHs (pH 3.5 to 6.0). Each sample was stored for up to 5 days at 5° C. or 50° C. The formulations were visually inspected for aggregation, and purity and potency were tested by strong cation exchange (SCX)-HPLC.

As shown in Table 3 below, none of the tested buffered exendin (9-39) formulations precipitated out of solution at 5° C. Within 48 hours at 50° C., the formulations at pH 4.5 and 5.0 showed visible aggregation, but for all other formulations no aggregation was visible.

TABLE 3

| Sample | Aggregates | |
|---|---|---|
| Formulation | 5° C. | 50° C. |
| 10 mM acetate, pH 3.5 | No | No |
| 10 mM acetate, pH 4.0 | No | Inconclusive |
| 10 mM acetate, pH 4.5 | No | Yes |
| 10 mM acetate, pH 5.0 | No | Yes |
| 10 mM acetate, pH 5.5 | No | No |
| 10 mM acetate, pH 6.0 | No | No |
| 20 mM acetate, pH 4.5 | No | Yes |
| 30 mM acetate, pH 4.5 | No | Yes |
| 10 mM citrate, pH 4.5 | No | Yes |

The formulations were analyzed by strong cation exchange-high performance liquid chromatography (SCX-HPLC) for purity and potency over a period of 5 days. The effects of storage at 50° C. for 5 days on the purity and potency of the exendin (9-39) buffered liquid formulations are shown in FIG. 2A and FIG. 2B.

Figure 2A:
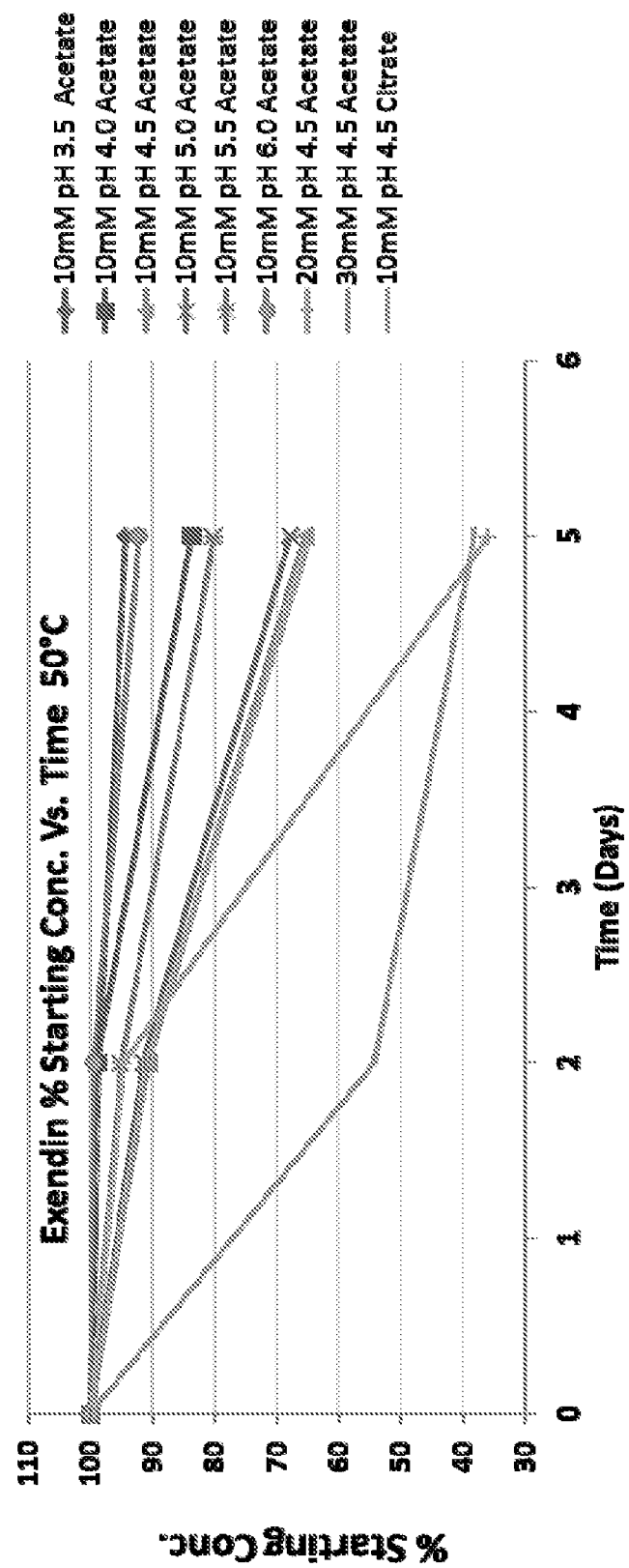
FIG. 2A-2B. Potency and purity data for exendin (9-39) formulations. (A) Graphical representation of potency data obtained for formulations comprising exendin (9-39) at a concentration equivalent to 15 mg/ml, prepared in acetate or citrate buffers having various ionic strengths, over a 5 day time course at 50° C. (B) Graphical representation of purity data obtained for formulations comprising exendin (9-39) at a concentration equivalent to 15 mg/ml, prepared in acetate or citrate buffers having various ionic strengths, over a 5 day time course at 50° C.
Figure 2B:
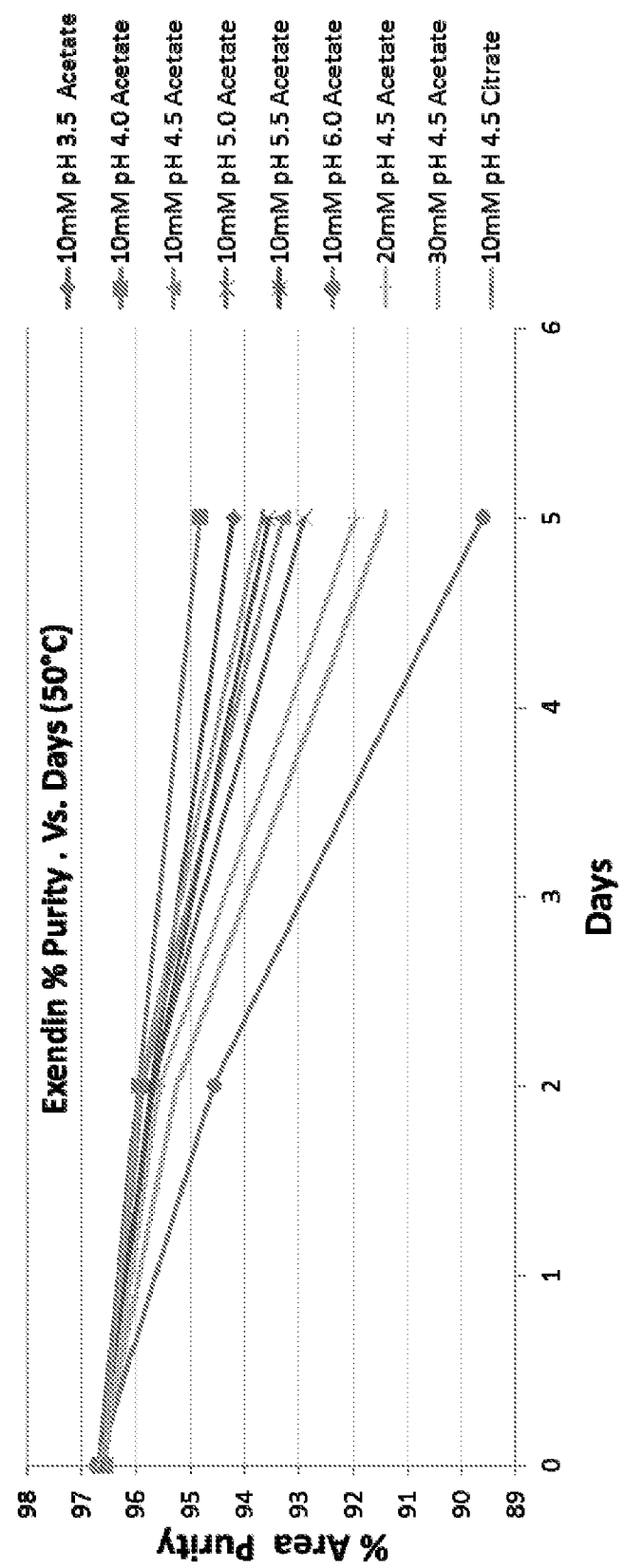

As shown in FIG. 2A and Table 4 below, citrate and acetate buffers were comparable with respect to the potency of exendin (9-39) at the end of the 5-day storage period. The least loss of exendin (9-39) (i.e., last impact on potency) was observed with pH 3.5 and pH 6.0. Higher buffer strength was associated with more loss of exendin (9-39) at the end of the 5-day period. As shown in FIG. 2B and Table 4, the least decrease in purity was observed for the formulation at a pH of 4.0, while the greatest decrease in purity was observed in the formulation at a pH of 6.0. Increasing the ionic buffer strength (e.g., from 10 mM to 20 mM or 30 mM) resulted in increased purity loss. The citrate and acetate buffers exhibited comparable activity.

The potency and purity of exendin (9-39) formulated in 10 mM acetate buffer at various pH after 5 days' storage at 50° C. is shown in FIG. 3. As shown in FIG. 3, the smallest decreases in exendin (9-39) were observed at a pH of 4.0 or lower or at a pH of 5.5 or higher. Potency loss was greatest where aggregation was visible (pH 4.5 and 5.0).

The impurity contributions were plotted against pH for exendin (9-39) formulated in 10 mM acetate buffer. FIG. 4 shows the effects of pH on impurities, measured as the % area contribution.

While not wishing to be bound by a particular theory, it is proposed that formulating exendin (9-39) in a buffer above the predicted isoelectric point of exendin (9-39) (pH 4.7) is advantageous because once the formulation is administered (e.g., injected), it does not pass through the isoelectric pH on the transition to the physiological pH of approximately 7.4. Additionally, formulating exendin (9-39) in a buffer at such a pH is expected to result in improved properties, such as improved potency, chemical stability, and less susceptibility to aggregation. In contrast, formulating exendin (9-39) in normal saline, which typically has a pH of about 4.5, may result in an increased likelihood of precipitation or aggregation because such a formulation must pass through the isoelectric pH of exendin (9-39) en route to physiological pH.

Example 2: Plasma Concentration Profile of Buffered Exendin (9-39) Formulations

This example shows that exendin (9-39) formulated in a buffer having a pH in the range of about 5-6 exhibits improved pharmacokinetic properties as compared to exendin (9-39) reconstituted in normal saline. For this example, exendin (9-39) acetate at a dose of 7.2 mg (equivalent to a dose of 30 mg in humans) was formulated in 10 mM sodium acetate and 45 mg/ml mannitol. The formulation had a pH of 5.5. The formulation was administered to dogs by subcutaneous injection at one of three concentrations: 15 mg/ml, 30 mg/ml, or 45 mg/ml (3 male dogs per group). The plasma concentration of exendin (9-39) was monitored after administration over a time course of 0 to 24 hours (FIG. 5B).

As a control, exendin (9-39) acetate at a dose of 7.2 mg (equivalent to a 30 mg dose in humans) was reconstituted in 0.9% normal saline having a pH of about 4.5 and administered subcutaneously to two dogs (1 male and 1 female).

TABLE 4

| | Conc. (mg/mL) | | | % Starting Potency | | | % Area Purity | | |
|---|---|---|---|---|---|---|---|---|---|
| Sample | Day 0 | Day 2 | Day 5 | Day 0 | Day 2 | Day 5 | Day 0 | Day 2 | Day 5 |
| 10 mM acetate, pH 3.5 | 4.93 | 4.87 | 4.66 | 100 | 98.8 | 94.4 | 96.6 | 95.7 | 94.2 |
| 10 mM acetate, pH 4.0 | 5.07 | 5.02 | 4.25 | 100 | 99.0 | 83.7 | 96.7 | 96.0 | 94.8 |
| 10 mM acetate, pH 4.5 | 5.10 | 4.63 | 3.34 | 100 | 90.8 | 65.6 | 96.6 | 95.9 | 93.3 |
| 10 mM acetate, pH 5.0 | 4.96 | 4.54 | 3.36 | 100 | 91.5 | 67.8 | 96.6 | 95.7 | 92.9 |
| 10 mM acetate, pH 5.5 | 5.00 | 4.75 | 4.01 | 100 | 95.1 | 80.2 | 96.7 | 95.7 | 93.6 |
| 10 mM acetate, pH 6.0 | 4.64 | 4.62 | 4.28 | 100 | 99.5 | 92.3 | 96.7 | 94.6 | 89.6 |
| 20 mM acetate, pH 4.5 | 5.12 | 4.85 | 1.84 | 100 | 94.8 | 35.9 | 96.6 | 95.6 | 92.0 |
| 30 mM acetate, pH 4.5 | 5.08 | 2.76 | 1.94 | 100 | 54.3 | 38.2 | 96.7 | 95.3 | 91.4 |
| 10 mM citrate, pH 4.5 | 5.06 | 4.61 | 3.27 | 100 | 91.1 | 64.6 | 96.6 | 95.9 | 93.7 |

Figure 5A:
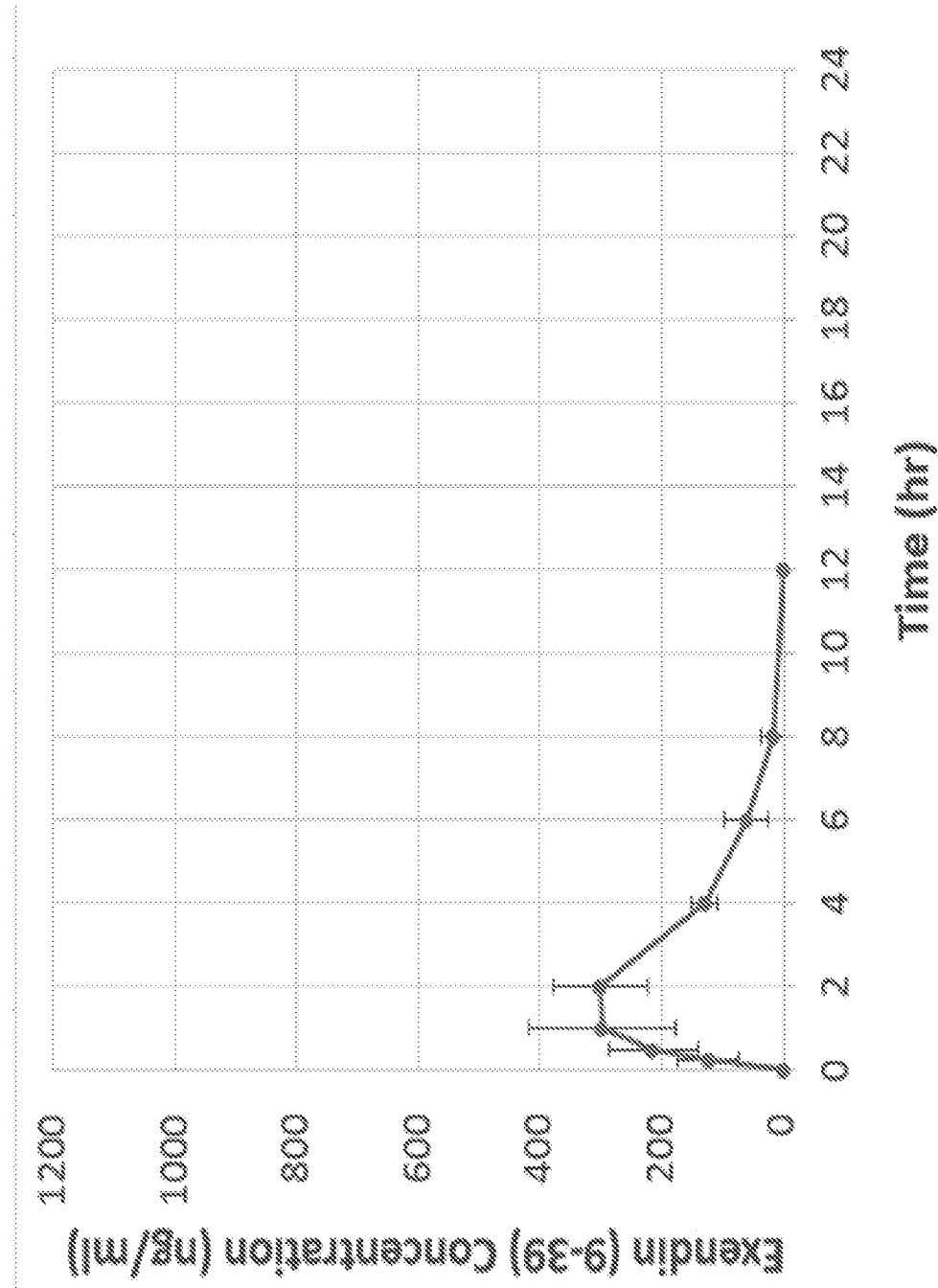
FIG. 5A-5B. Plasma pharmacokinetic profile of formulations comprising exendin (9-39). (A) Plasma pharmacokinetic profile of exendin (9-39) acetate powder formulated in 0.9% normal saline delivered by subcutaneous administration to dogs at 0.72 mg/kg (total dose of 7.2 mg, equivalent to 30 mg human dose). (B) Plasma pharmacokinetic profile of exendin (9-39) acetate (total dose 7.2 mg) formulated in 10 mM sodium acetate buffer at a pH of 5.5 and comprising 45 mg/mL mannitol delivered by subcutaneous administration to dogs at a concentration of exendin (9-39) equivalent to 15 mg/ml, 30 mg/ml, or 45 mg/ml in humans.
Figure 5B:
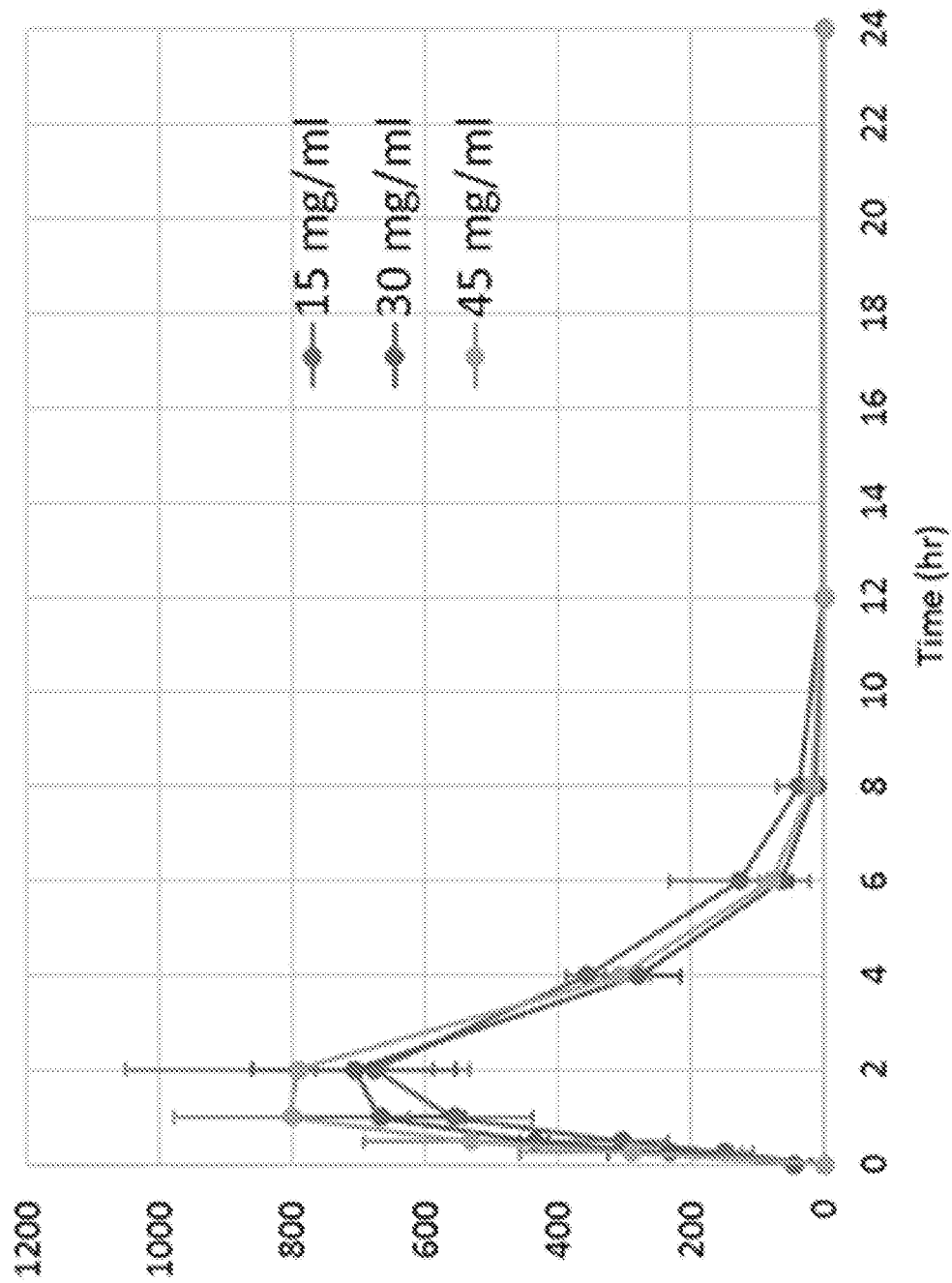

FIG. 5A shows the resulting plasma concentration profile obtained by administering exendin (9-39) reconstituted in 0.9% normal saline.

As can be seen by comparison of FIG. 5A and FIG. 5B, the buffered liquid formulations (comprising exendin (9-39) and 45 mg/ml mannitol in 10 mM sodium acetate and having a pH of 5.5), at all concentrations tested, resulted in a higher plasma concentration of exendin (9-39) over the first 4 hours after administration as compared to the lyophilized exendin (9-39) reconstituted in normal saline.

Example 3: Repeat Subcutaneous Dosing of Exendin 9-39 Reduces Hyperinsulinemic Hypoglycemia and Neuroglycopenic Symptoms in Patients with Post-Bariatric Hypoglycemia Abstract Post-Bariatric Hypoglycemia (PBH) is a rare but serious complication of bariatric surgery manifested by frequent episodes of symptomatic postprandial hypoglycemia, for which there are no approved pharmacotherapies. A central role for exaggerated meal-induced secretion of the incretin hormone, glucagon-like peptide-1 (GLP-1) with dysregulated insulin secretion has been established, making GLP-1 receptor antagonism an attractive and targeted therapeutic approach. Studies evaluating the use of a single intravenous (IV) infusion or subcutaneous (SC) injection of the GLP-1 receptor antagonist exendin (9-39) have demonstrated that a single dose of exendin (9-39) can prevent postprandial hypoglycemia, normalize beta cell function, and reduce neuroglycopenic symptoms in patients with PBH during oral glucose tolerance testing (OGTT).

This multiple-ascending dose (MAD) study evaluated the efficacy, tolerability, and pharmacokinetic profile of two formulations of exendin (9-39) subcutaneously administered over up to 3 days BID in participants with PBH. In Part A of this two-part study, 14 participants with PBH underwent a baseline OGTT followed by multiple ascending doses of up to 3 days of BID lyophilized exendin (9-39) reconstituted in 0.9% normal saline ("Lyo") with a repeat OGTT on the final day of dosing. In Part B of this study, 5 participants underwent 3 days of BID treatment with a buffered liquid formulation comprising 30 mg exendin (9-39) and 45 mg/ml mannitol in 10 mM sodium acetate at a pH of 5.5 ("Liq"). Repeat dosing of both formulations of SC exendin (9-39) were well tolerated, improved postprandial hyperinsulinemic hypoglycemia, and reduced associated symptoms in patients with PBH in a dose-dependent manner. The buffered liquid exendin (9-39) formulation improved postprandial metabolic and clinical parameters with comparable or greater efficiency than the lyophilized exendin (9-39) reconstituted in saline, and also appeared to confer greater exposure and duration of action. In conclusion, buffered liquid exendin (9-39) formulations represent a promising, convenient formulation for subcutaneous administration of exendin (9-39), and may provide an opportunity for lower and/or less frequent dosing.

Background

PBH is a rare but serious complication of bariatric surgery manifested by frequent episodes of symptomatic postprandial hypoglycemia, for which there are no approved pharmacotherapies. A central role for exaggerated meal-induced secretion of the incretin hormone, glucagon-like peptide-1 (GLP-1) with dysregulated insulin secretion has been established, making GLP-1 receptor antagonism an attractive and targeted therapeutic approach. Studies evaluating IV infusion (Salehi et al., *Gastroenterology*, 2014, 146:669-680; Craig et al., *Diabetologia*, 2017, 60:531-540) or SC injection of the GLP-1 receptor antagonist Ex-9-39 (see, WO 2016/191395) have demonstrated that a single dose of exendin (9-39) can prevent postprandial hypoglycemia, normalize beta cell function, and reduce neuroglycopenic symptoms in patients with PBH during OGTT. The current trial represents the first assessment in humans of subcutaneously administered exendin (9-39) formulated in a buffered liquid formulation. We present interim results (19 of 20 participants) from this investigation aimed at evaluating the efficacy, tolerability, and pharmacokinetic profile of multiple ascending doses of two formulations of subcutaneously administered exendin (9-39) (lyophilized exendin (9-39) reconstituted in saline, or exendin (9-39) in a buffered liquid formulation) administered for up to 3 days BID in participants with PBH.

Methods

Figure 6:
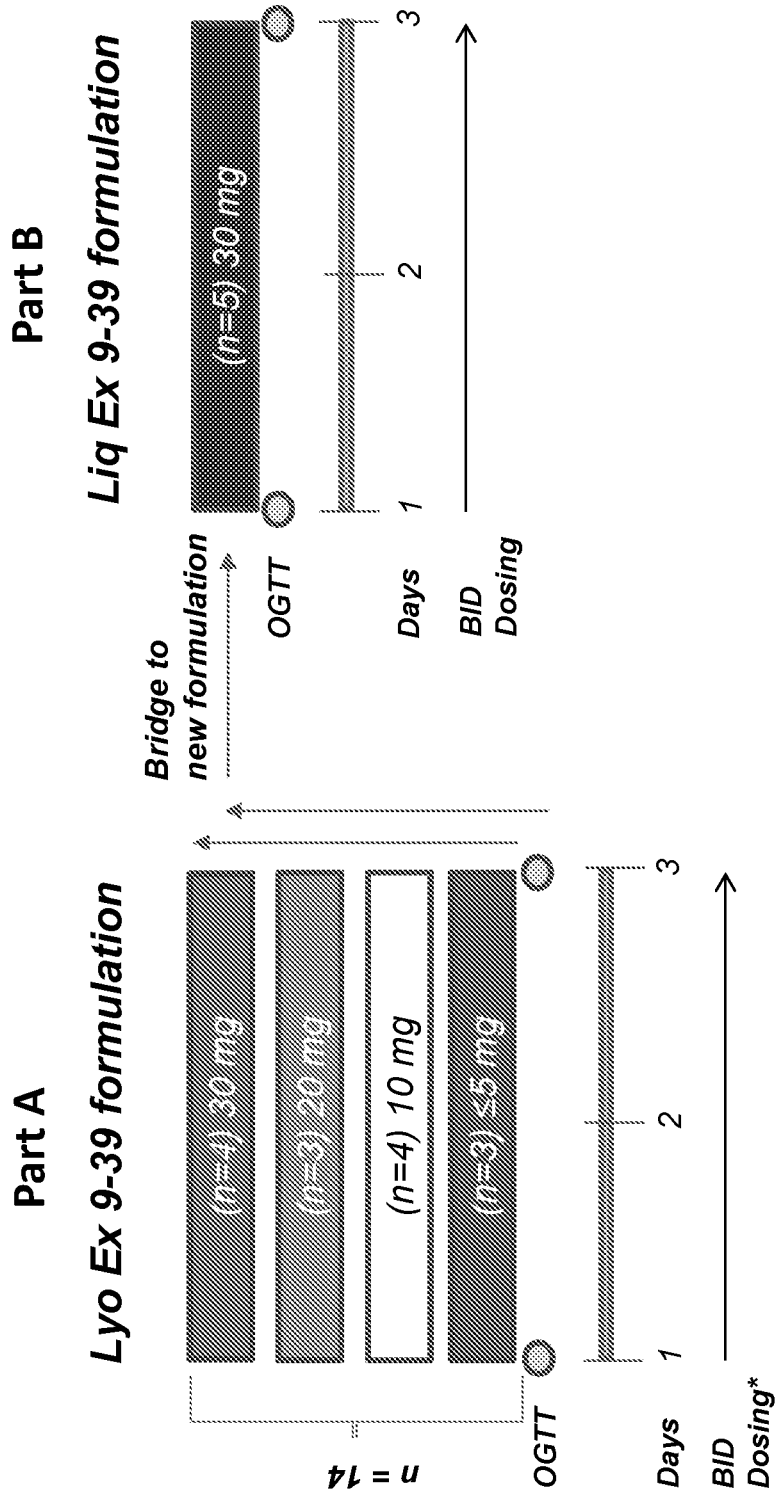
FIG. 6. Schematic of study, including number of participants for each of the reconstituted lyophilized exendin (9-39) ("Part A") and buffered liquid exendin (9-39) ("Part B") formulations, dosing, and oral glucose tolerance test time points.

Study Design and Procedures:

This Phase 2 MAD study was conducted in two parts, Parts A and B. In Part A, 14 participants underwent a baseline OGTT, followed by up to 3 days of BID doses of a reconstituted lyophilized formulation of exendin (9-39) ("Lyo") ranging from 2.5-32 mg with a repeat OGTT on the final day of dosing. In Part B, 5 participants underwent a baseline OGTT, followed by 30 mg BID of exendin (9-39) formulated in a liquid buffer comprising 10 mM sodium acetate and 45 mg/ml mannitol and having a pH of 5.5 ("Liq") with a repeat OGTT on Day 3 of treatment (See FIG. 6). In both parts, metabolic, clinical, and pharmacokinetic responses were evaluated, and tolerability and safety were monitored. Determination of dose levels and frequency were based upon interim review of PK, PD, and safety data. Symptoms of hypoglycemia were assessed during each OGTT by use of the Edinburgh Hypoglycemia Symptom Scale (EHSS) (4,5). At a plasma glucose of 50 mg/dL the OGTT was stopped with investigator rescue by IV dextrose.

Study Participants:

Eligible participants were men or women, ages 18 to 65 years, who had undergone Roux-en-Y gastric bypass (RYGB) surgery at least 12 months prior, with a documented history of Whipple's triad, with inappropriately elevated insulin concentrations (>3 µU/mL) at the time of hypoglycemia 55 mg/dL) and a minimum of one symptomatic episode per month by patient report. Characteristics of the 14 study participants are provided in Table 5, below.

TABLE 5

| Characteristic | Lyophilized Ex 9-39 formulation n = 14 | Buffered liquid Ex 9-39 formulation n = 5 |
|---|---|---|
| Age (years) | 45 ± 3.5 | 51 ± 2.9 |
| Sex (male/female) | 0/13 | 0/5 |
| Pre-surgical BMI (kg/m$^2$) | 48 ± 2.1 | 50 ± 2.4 |
| Postsurgical BMI (kg/m$^2$) | 28 ± 1.0 | 30 ± 2.3 |
| Postsurgical time to hypoglycemia (y) | 2.0 ± 0.5 | 1.8 ± 0.9 |
| Postsurgical time with hypoglycemia (y) | 6.6 ± 1.2 | 8.4 ± 1.1 |
| History of T2D (yes/no) | 3/10 | 1/5 |
| HOMA-IR (U) | 35 ± 6 | 40 ± 9 |
| Percent with postprandial BG < 50 mg/dl at least daily | 54 | 60 |
| Percent with neuroglycopenia at least daily | 54 | 60 |

Figure 7B:
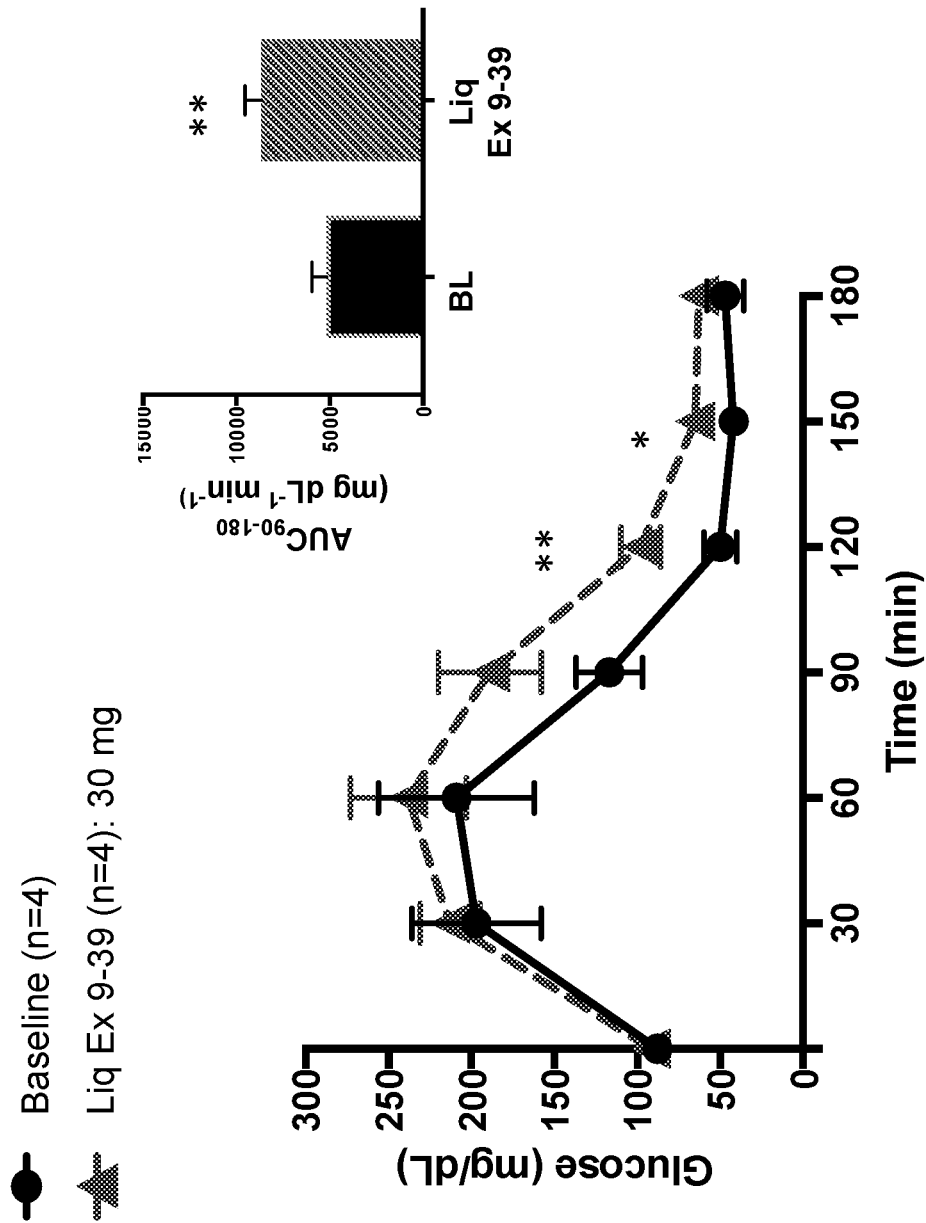
Figure 7C:
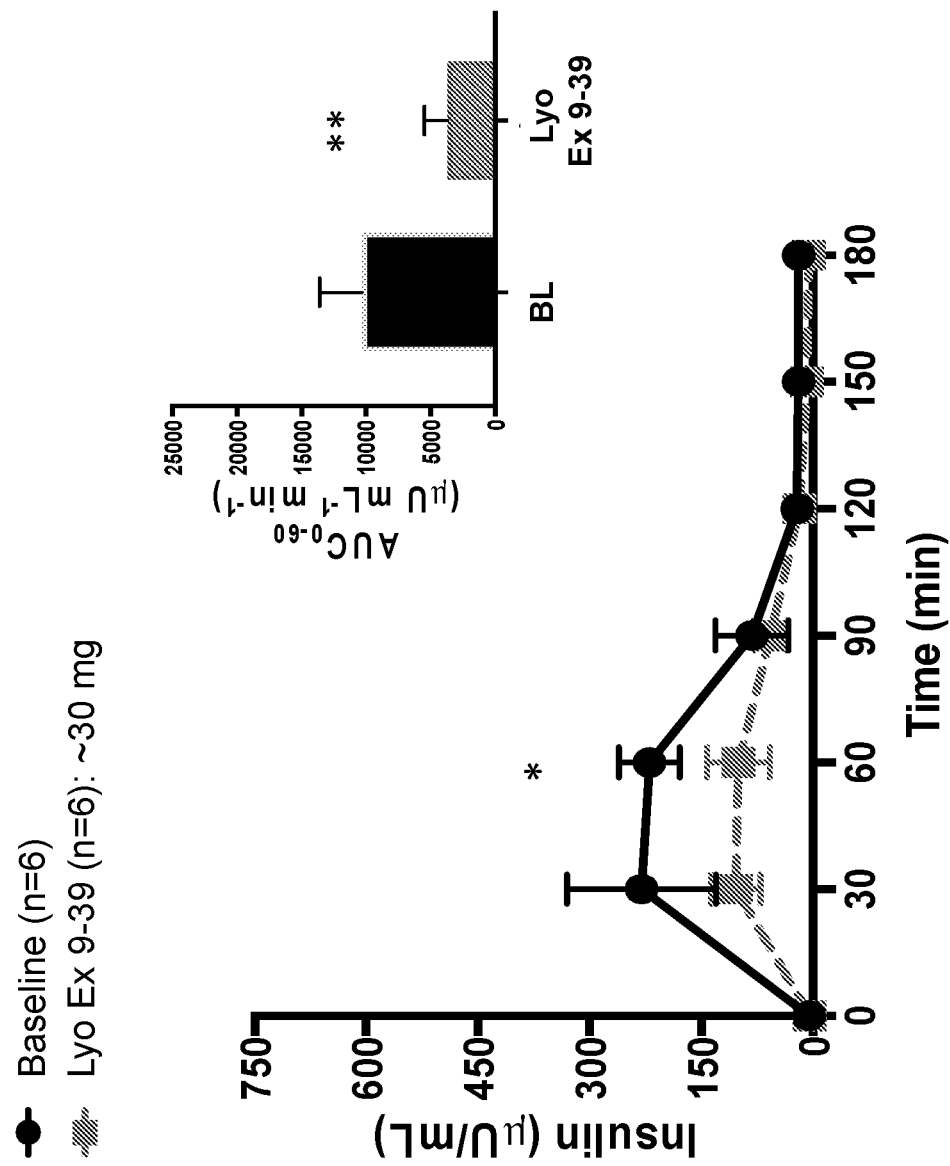
Figure 7D:
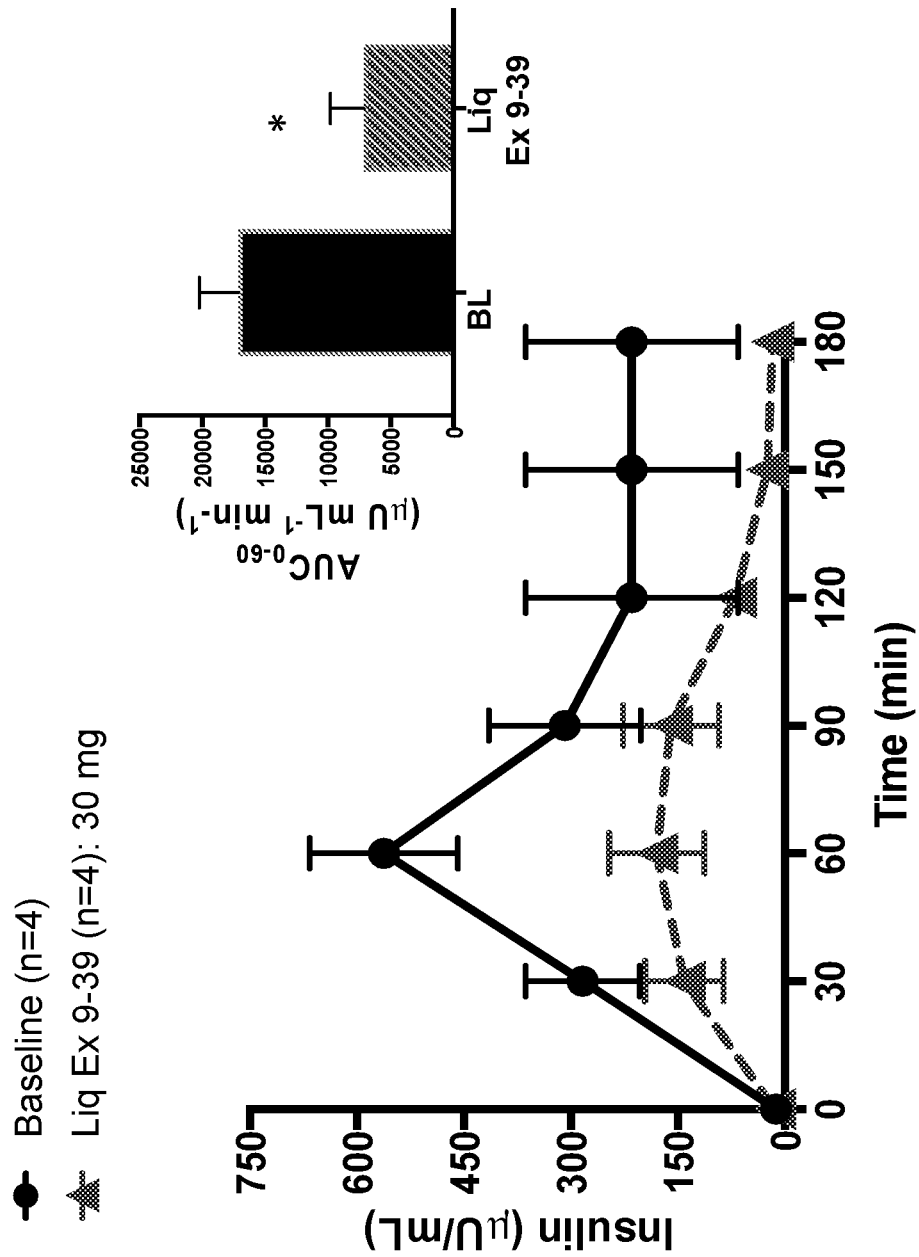
Figure 8B:
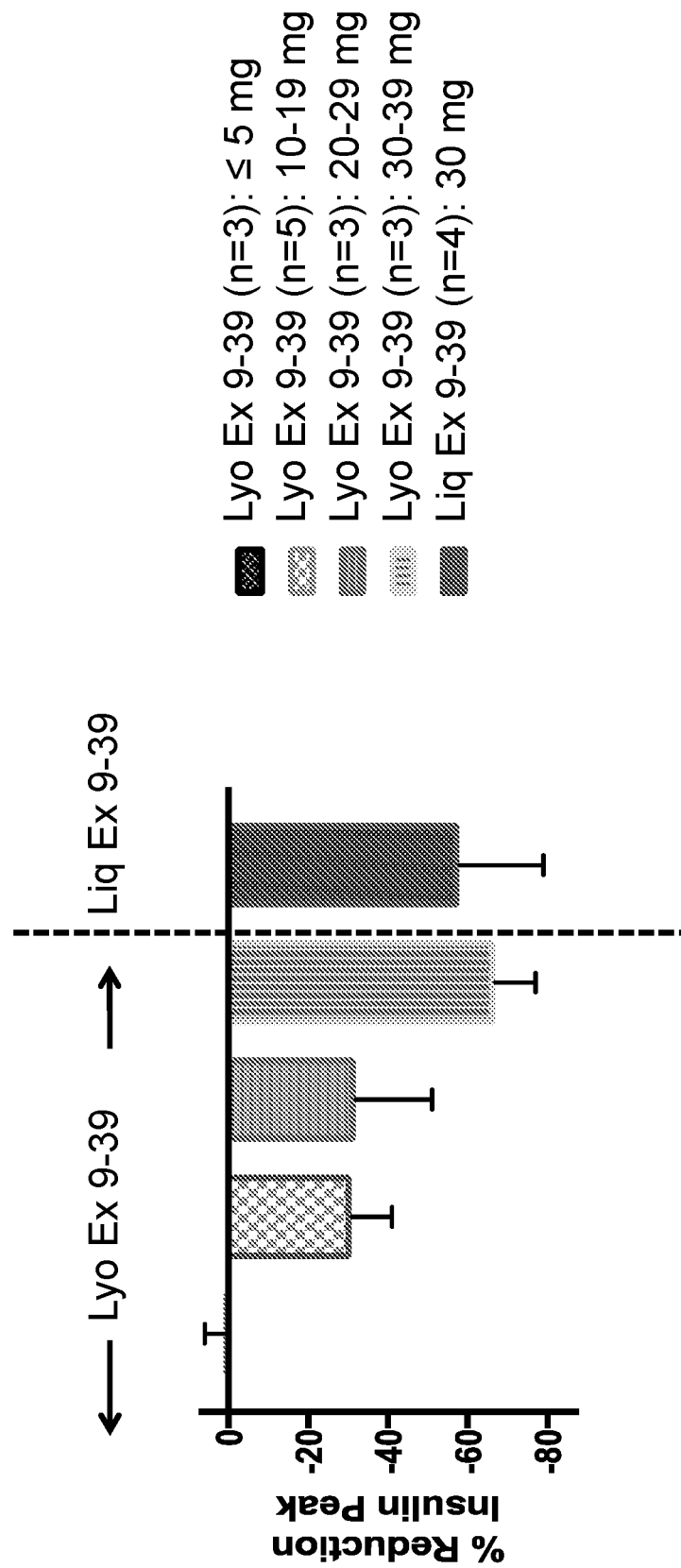

BMI = body mass index;
HOMA-IR = homeostatic model assessment of insulin resistance;
T2D = type 2 diabetes Results
Metabolic and Clinical Responses:
Part A: Treatment with a reconstituted lyophilized formulation of exendin (9-39) reduced the presence and degree of hypoglycemia at all dose levels. Participants receiving doses of 18 mg did not require IV dextrose rescue. A dose-response relationship was observed for reconstituted lyophilized exendin (9-39) with incrementally increasing improvements in glucose nadir, insulin peak, and symptom score (FIGS. 8A-8C and Table 6 below). The top two dose cohorts, who on average received approximately 30 mg reconstituted lyophilized exendin (9-39) BID over 3 days, demonstrated a mean 37% increase in glucose nadir, 50% reduction in peak insulin concentrations, and 50% reduction in overall hypoglycemia symptom score, with a 50% reduction in neuroglycopenic symptoms (FIGS. 7A and 7C and Table 6 below). All doses were well tolerated with only mild headache or nausea reported, and no drug related adverse events (DRAEs) observed.

On the basis of the interim efficacy, safety, and tolerability results, a fixed dose of 30 mg BID of exendin (9-39) buffered liquid formulation was selected for Part B.

Part B: Treatment with BID doses of 30 mg exendin (9-39) buffered liquid formulation raised the postprandial glucose nadir during OGTT on the third day of dosing in all participants evaluated, with none requiring IV dextrose rescue. On average, participants achieved a 49% increase in glucose nadir, a 58% reduction in peak insulin concentrations, and a 56% reduction in overall hypoglycemia symptom score, and a 12% reduction in neuroglycopenic symptoms (FIGS. 7B, 7D, 8A-8C). All doses were well tolerated with no DRAEs observed.

Figure 9A:
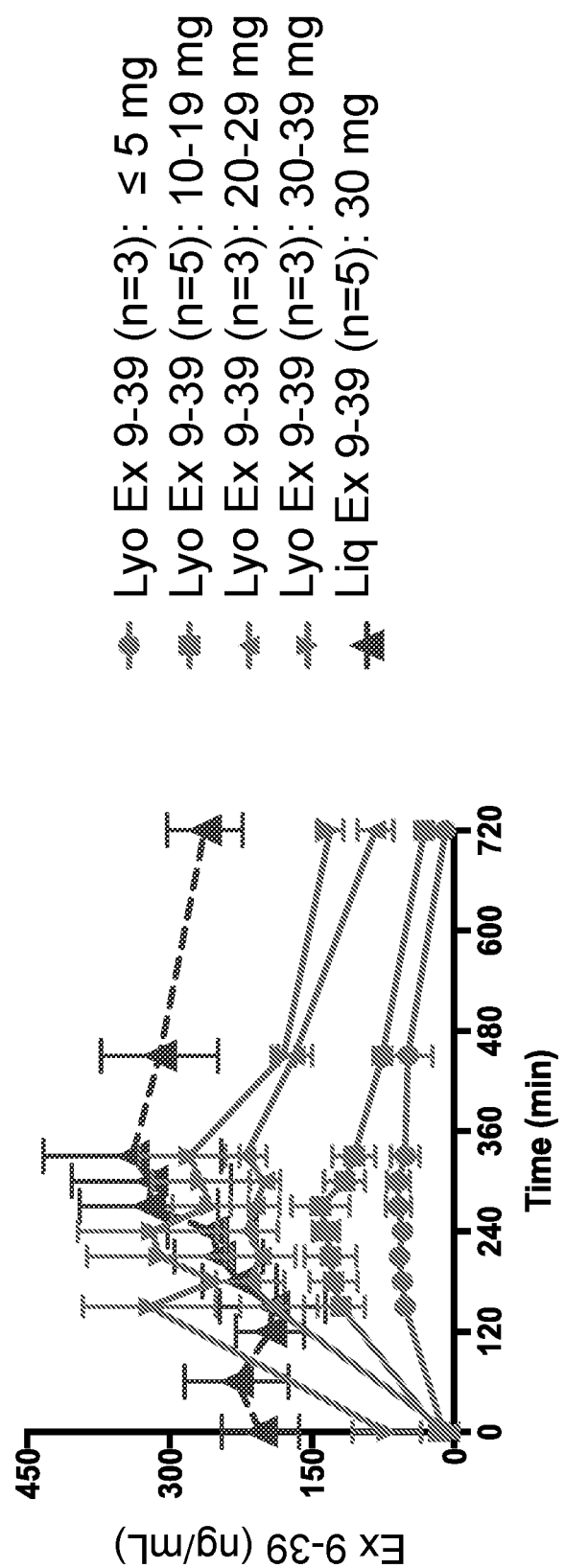
FIG. 9A-9B. Pharmacokinetic profiles for formulations comprising exendin (9-39). (A) 12-hour pharmacokinetic profiles by dose and formulation in 19 PBH subjects on the final day of multiple ascending doses of lyophilized exendin (9-39) reconstituted in saline ("Lyo Ex 9-39") (red) or a 30 mg buffered liquid exendin (9-39) formulation ("Liq Ex 9-39") (blue). Plasma concentration (mean±SEM) versus time by dose in mg. (B) AUC exendin (9-39) concentrations by dose and formulation in 19 PBH subjects on the final day of multiple ascending doses of Lyo Ex 9-39 (red) or Liq Ex 9-39 (blue). Individual plasma AUC concentrations versus dose in mg/kg.
Figure 9B:
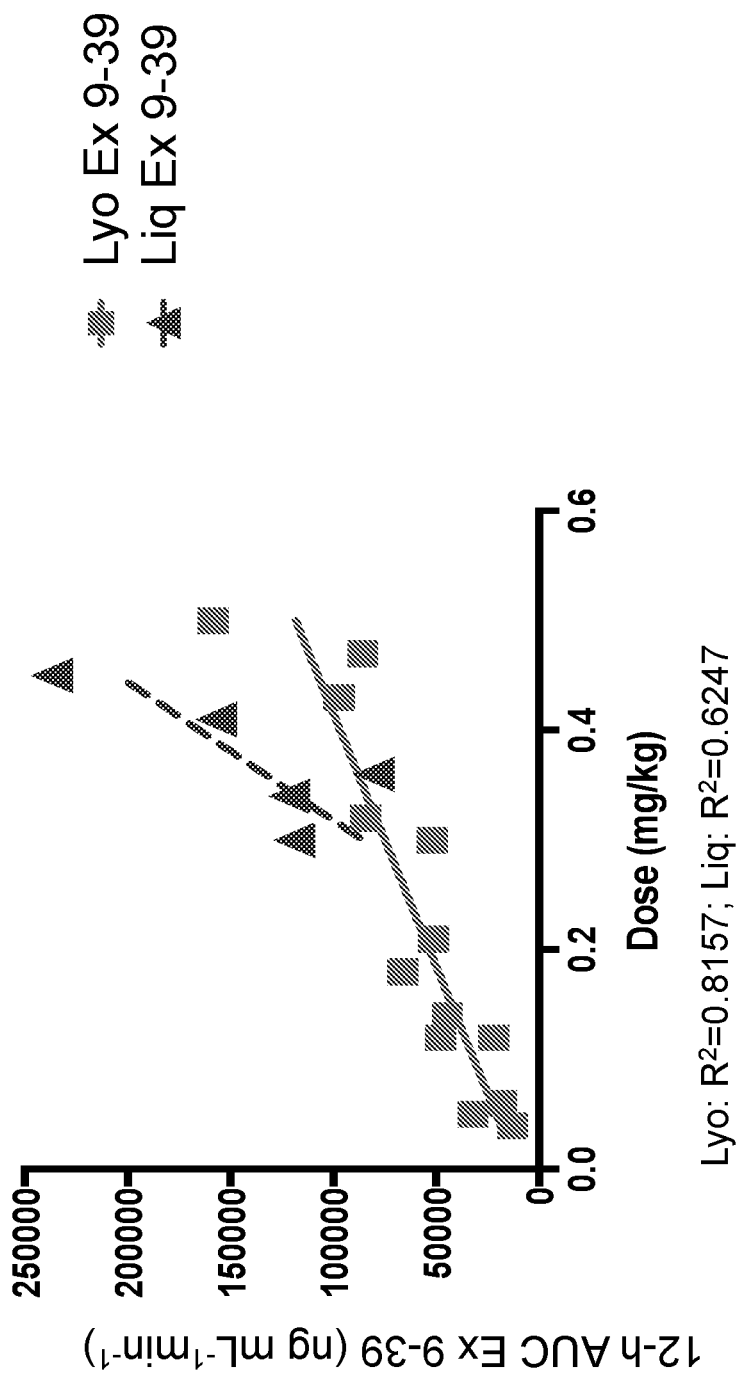

Pharmacokinetic Responses:
Part A: Increasing doses of reconstituted lyophilized exendin (9-39) resulted in incrementally increased exendin (9-39) exposure, as demonstrated by $C_{max}$ and 12-hour AUC concentrations (FIGS. 9A-9B and Table 6).

Part B: Equivalent doses administered on a mg/kg basis of exendin (9-39) buffered liquid formulation, vs reconstituted lyophilized exendin (9-39), yielded a higher $C_{max}$, a higher 12-hour AUC, and a later $T_{max}$. The exendin (9-39) buffered liquid formulation resulted in higher trough plasma concentrations on the final day of dosing and demonstrated a more sustained absorption profile than comparable doses of reconstituted lyophilized exendin (9-39) (FIGS. 9A-9B and Table 6).

TABLE 6

| Dose (mg) | Lyo Ex 9-39 | | | | Liq Ex 9-39 |
| --- | --- | --- | --- | --- | --- |
| | ≤5 mg | 10-19 mg | 20-29 mg | 30-39 mg | 30 mg |
| Number of participants | 3 | 5 | 3 | 3 | 5 |
| Dose administered (mg/kg) | 0.05 ± 0.1 | 0.15 ± 0.02 | 0.35 ± 0.04 | 0.46 ± 0.02 | 0.38 ± 0.03 |
| Metabolic responses | | | | | |
| Glucose (mg/dL) | | | | | |
| Nadir | 45 ± 4 | 46 ± 5 | 51 ± 2 | 59 ± 8 | 60 ± 7 |
| % increase nadir | 16 | 6 | 33 | 41 | 49 |
| % increase $AUC_{90.180}$ | 42 | 23 | 57 | 101 | 73 |
| Rescue required | Yes | Yes | No | No | No |
| Insulin (μU/mL) | | | | | |
| % reduction peak | −1 | 31 | 32 | 67 | 58 |
| % reduction $AUC_{0.60}$ | −20 | 44 | 26 | 68 | 56 |
| Pharmacokinetic responses | | | | | |
| $C_{max}$ (ng/mL) | 61 ± 12 | 156 ± 24 | 228 ± 33 | 331 ± 72 | 359 ± 87 |
| $T_{max}$ (min) | 270 ± 17 | 252 ± 7 | 240 ± 35 | 190 ± 26 | 396 ± 82 |
| $AUC_{0.720}$(min ng/mL) | 21151 ± 5702 | 46485 ± 7105 | 77981 ± 13522 | 113872 ± 22599 | 142971 ± 26449 |

Subjects received multiple ascending doses of lyophilized (Lyo) and/or liquid (Liq) Ex 9-39;
Data presented as % change from baseline or mean ± standard error of the mean (SEM)

Conclusions

In patients with refractory PBH repeat dosing of subcutaneously administered exendin (9-39) produced the following results during OGTT provocation: (1) Dose-dependent improvements in postprandial hyperinsulinemic hypoglycemia, and substantial reductions in the associated symptoms; (2) Prevention of neuroglycopenia with no need for rescue therapy at doses ≥18 mg; and (3) No drug related adverse events or tolerability concerns. Exendin (9-39) buffered liquid formulation, a ready-to-use formulation, provided at least comparable protection against symptomatic postprandial hyperinsulinemic hypoglycemia and may confer greater pharmacokinetic exposure with longer duration of action.

Example 4: Pharmacokinetic Profile of Single- and Multiple-Ascending Doses of a Subcutaneously Administered Buffered Exendin (9-39) Formulation A Phase 1 trial was conducted investigating the safety, tolerability, pharmacokinetic and pharmacodynamic profile of single- and multiple-ascending doses of a subcutaneously administered buffered liquid formulation of exendin (9-39). For this study, the exendin (9-39) was formulated at a concentration of 30 mg/ml in a liquid buffer comprising 10 mM sodium acetate and 45 mg/ml mannitol and having a pH of 5.5. In this single-center study in healthy volunteers, 32 subjects were subcutaneously administered either single ascending doses of exendin (9-39) ranging from 7.5 mg to 45 mg (24 volunteers) or placebo (8 volunteers) (Part A); and 16 subjects received 1 of 3 ascending doses (60, 75 or 90 mg of exendin (9-39) administered once daily for 3 consecutive days).

Within the single ascending dose group of Part A, 32 healthy subjects were enrolled into 4 successive cohorts of 8 subjects each as follows: 6 subjects received exendin (9-39) at doses of 7.5, 15, 30 or 45 mg and 2 subjects received placebo in each cohort. Within the multiple ascending doses group of Part B, 16 healthy subjects were enrolled in 3 successive cohorts of 6, 6 and 4 subjects that received 1 of 3 dose levels of 60, 75 or 90 mg, respectively, of exendin (9-39) administered once daily for 3 consecutive days.

As shown in Table 7 below and FIG. 10A, mean systemic exposure ($C_{max}$, $AUC_{0-tau}$ and $AUC_{0-inf}$) increased with dose in an approximately dose-proportional manner.

a higher dose, such as 60 mg QD, may provide therapeutic plasma concentrations for approximately 16 hours for patients requiring a higher systemic exposure and/or patients preferring the convenience of a once-a-day regimen. Under a once daily dosing regimen, it may be preferred to have at least a 60-minute delay after dosing prior to the morning meal, and to avoid eating in the late evening. Therefore, a

TABLE 7

Average Pharmacokinetic Results by Treatment Day After Administration of Exendin (9-39) Doses Ranging from 7.5 to 90 mg

| Part | Study Day | Cohort | No. Subj. | Dose (mg) | $C_{max}$ (ng/mL) | $T_{max}$ (h) | $C_{min}$ (ng/mL) | HL (h) | $\lambda_z$ (1/h) | $AUC_{0-tau}$ (ng · h/mL) | $AUC_{0-inf}$ (ng · h/mL) | CL (L/h) | VoD (L) |
|---|---|---|---|---|---|---|---|---|---|---|---|---|---|
| A | 1 | S1 | 6 | 7.5 | 67 | 5.6 | 19 | 6.9 | 0.10 | 769 | 803 | 9.5 | 101 |
| A | 1 | S2 | 6 | 15 | 132 | 6.7 | 21 | 5.2 | 0.14 | 1615 | 1643 | 9.5 | 75 |
| A | 1 | S3 | 6 | 30 | 295 | 8.5 | 28 | 4.7 | 0.17 | 3364 | 3397 | 9.2 | 65 |
| A | 1 | S4 | 6 | 45 | 509 | 7.0 | 51 | 5.3 | 0.17 | 5553 | 5592 | 8.3 | 68 |
| B | 1 | M1 | 6 | 60 | 647 | 7.0 | 55 | 2.6 | 0.29 | 7487 | 7503 | 8.1 | 31 |
| B | 3 | M1 | 6 | 60 | 704 | 7.5 | 53 | 2.8 | 0.33 | 7829 | 7846 | 7.8 | 31 |
| B | 1 | M2 | 6 | 75 | 684 | 7.7 | 91 | 2.9 | 0.26 | 8823 | 8838 | 8.7 | 36 |
| B | 3 | M2 | 6 | 75 | 742 | 7.2 | 71 | 3.1 | 0.24 | 8923 | 8945 | 8.5 | 38 |
| B | 1 | M3 | 4 | 90 | 772 | 7.8 | 88 | 3.0 | 0.25 | 9475 | 9485 | 9.7 | 43 |
| B | 3 | M3 | 4 | 90 | 775 | 7.0 | 100 | 2.9 | 0.27 | 9427 | 9465 | 9.7 | 43 |

$C_{max}$: maximum observed plasma concentration, $T_{max}$: time of maximum observed concentration, $C_{min}$: minimum observed plasma concentration, HL: half-life, $\lambda_z$: apparent elimination rate constant, $AUC_{0-tau}$: area under the plasma concentration curve to tau, $AUC_{0-inf}$: area under the plasma concentration curve extrapolated to infinity, CL: clearance, VoD: volume of distribution.

Figure 10A:
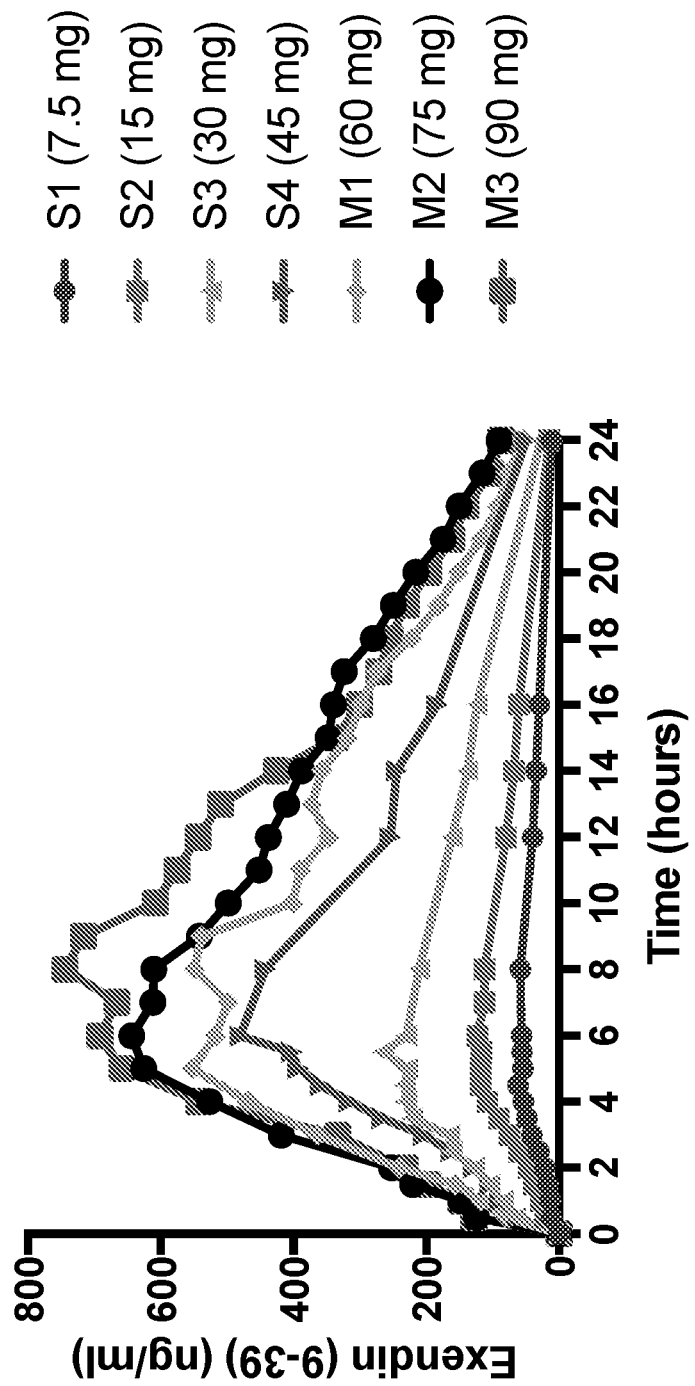
FIG. 10A-10B. 24-hour pharmacokinetic profiles for formulations comprising exendin (9-39). (A) PK profile after single subcutaneous dose of buffered liquid exendin (9-39) formulation in doses ranging from 7.5-90 mg. Plasma concentration (mean) versus time by dose in mg. S1=single ascending dose study, 7.5 mg dose; S2=single ascending dose study, 15 mg dose; S3=single ascending dose study, 30 mg dose; S4=single ascending dose study, 45 mg dose; M1=multiple ascending doses study, 60 mg dose; M2=multiple ascending doses study, 75 mg dose; M3=multiple ascending doses study, 90 mg dose. (B) Pharmacokinetic profile after multiple subcutaneous doses of buffered liquid exendin (9-39) formulation after 3 days of 30 mg BID dosing (Stanford MAD study of Example 3) and after 60 mg QD dosing (Phase 1 study of Example 4).
Figure 10B:
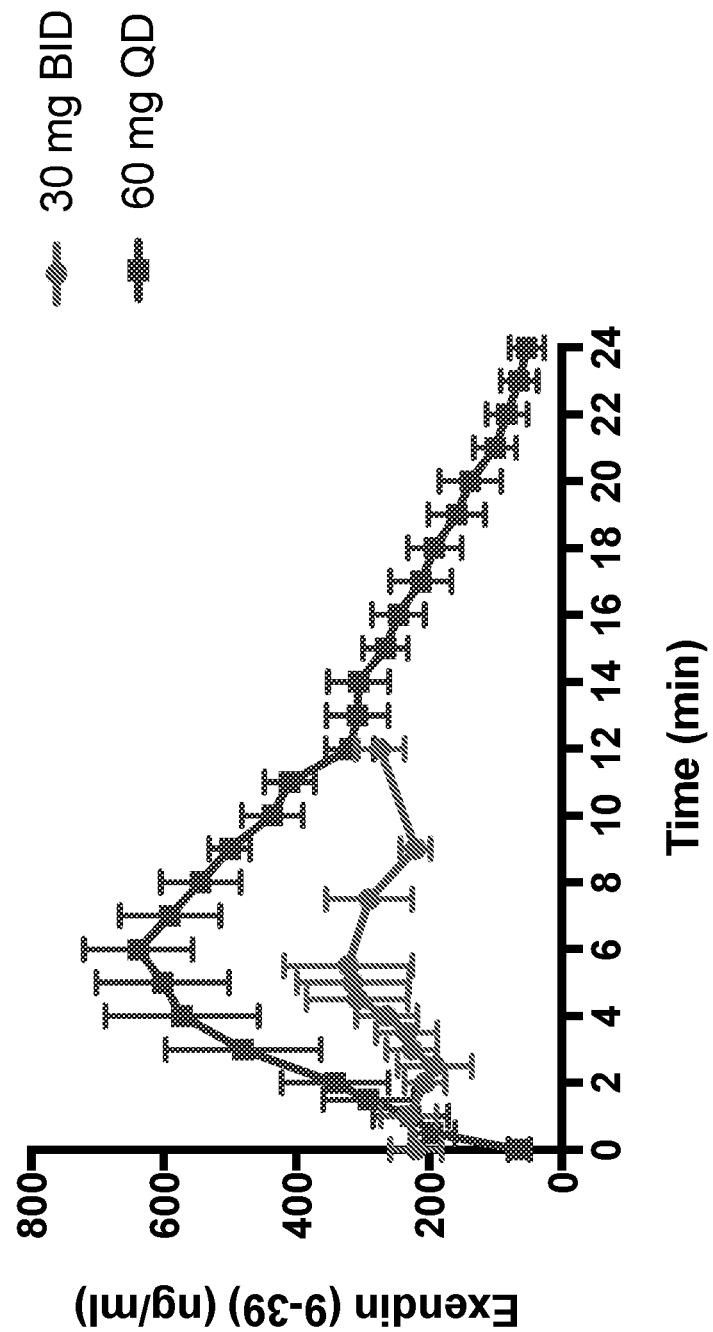

As shown in FIG. 10B, pre-dose trough plasma concentrations on Day 3 of 30 mg BID dosing approached plasma concentrations of exendin (9-39) that are expected to be therapeutic (>220 ng/ml), with relatively sustained plasma concentrations throughout the daytime hours (prior to next dosing time T=12 hours). Within 60 minutes of a 60 mg AM dose administration, the target expected therapeutic concentrations (>220 ng/ml) were achieved, with higher peak plasma concentrations and sustained therapeutic concentrations observed throughout the daytime hours.

The dose levels and dosing interval of exendin (9-39) for a planned Phase 2 Study were selected based on results from this Phase 1 Study (e.g., as shown in Table 7 and FIGS. 10A-10B) as well as results from a completed MAD study in PBH patients conducted at Stanford University. In the Stanford MAD study, patients with refractory PBH experienced significant improvements in glucose nadir and neuroglycopenic symptoms during oral glucose tolerance testing after dosing with 30 mg BID of exendin (9-39), with improved postprandial metabolic and clinical parameters after the buffered liquid formulation as compared to the lyophilized exendin (9-39) reconstituted in saline. In the Stanford MAD study, optimal pharmacodynamic effects (postprandial glucose nadir >50 mg/dl and decrease in peak insulin of at least 50%) were achieved with peak plasma concentrations ($C_{max}$) of at least 220 ng/ml. In contrast, in the investigation described herein (e.g., as shown in this example and in Example 3), the buffered liquid formulation demonstrated greater pharmacokinetic and pharmacodynamic efficiency as compared to the reconstituted lyophilized exendin (9-39) formulated in normal saline.

Together, the PK data from this Phase 1 study in healthy volunteers as shown in Table 7 and FIGS. 10A-10B, and the PK and PD data from the completed Stanford MAD study as described in Example 3, suggest that repeat subcutaneous dosing of 30 mg BID of the buffered liquid formulation may provide sufficient plasma concentrations of exendin (9-39) to confer protection against postprandial hypoglycemia without the need to wait to eat after dosing. The data also suggest that the prolonged and higher exposure conferred by a total daily dose of 60 mg (administered subcutaneously as either 30 mg every 12 hours or 60 mg every morning) was selected for an upcoming Phase 2 study in patients with refractory PBH.

Although the foregoing invention has been described in some detail by way of illustration and example for purposes of clarity of understanding, one of skill in the art will appreciate that many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with the true scope and spirit of the invention being indicated by the following claims.

All publications, patents, patent applications or other documents cited herein are hereby incorporated by reference in their entirety for all purposes to the same extent as if each individual publication, patent, patent application, or other document was individually indicated to be incorporated by reference for all purposes.

What is claimed is:

1. A liquid pharmaceutical formulation comprising exendin (9-39) or a pharmaceutically acceptable salt thereof and a tonicity modifier in a physiologically acceptable buffer having a pH in the range of above 5.1 to 6, wherein the exendin (9-39) or the pharmaceutically acceptable salt thereof does not exhibit detectable aggregation in the formulation, and wherein the liquid pharmaceutical formulation, when administered to a human subject, has an improved pharmacokinetic profile as compared to a composition comprising the same dose of exendin (9-39) or a pharmaceutical acceptable salt thereof formulated in 0.9% normal saline.

2. The liquid pharmaceutical formulation of claim 1, wherein the physiologically acceptable buffer comprises an acetate buffer or a citrate buffer.

3. The liquid pharmaceutical formulation of claim 1, wherein the physiologically acceptable buffer comprises sodium acetate or sodium citrate.

4. The liquid pharmaceutical formulation of claim 1, wherein the physiologically acceptable buffer comprises sodium acetate or sodium citrate at a concentration from about 5 mM to about 30 mM.

5. The liquid pharmaceutical formulation of claim 1, wherein the physiologically acceptable buffer comprises sodium acetate at a concentration of about 10 mM.

6. The liquid pharmaceutical formulation of claim 1, wherein the buffer has a pH in the range of 5.2 to 5.8.

7. The liquid pharmaceutical formulation of claim 6, wherein the pH is about 5.5.

8. The liquid pharmaceutical formulation of claim 1, wherein the tonicity modifier comprises mannitol, dextrose, glycerin, lactose, sucrose, or trehalose.

9. The liquid pharmaceutical formulation of claim 8, wherein the tonicity modifier comprises mannitol.

10. The liquid pharmaceutical formulation of claim 8, wherein the tonicity modifier is present in an amount from about 20 mg/ml to about 60 mg/ml.

11. The liquid pharmaceutical formulation of claim 10, wherein the tonicity modifier is present in an amount that achieves an osmolality of 290 mOsm/kg.

12. The liquid pharmaceutical formulation of claim 1, wherein the pharmaceutically acceptable salt of exendin (9-39) is exendin (9-39) acetate or exendin (9-39) trifluoroacetate.

13. The liquid pharmaceutical formulation of claim 1, wherein the exendin (9-39) or the pharmaceutically acceptable salt thereof is at a concentration of about 10 mg/ml to about 120 mg/ml.

14. The liquid pharmaceutical formulation of claim 13, wherein the exendin (9-39) or the pharmaceutically acceptable salt thereof is at a concentration of at least 15 mg/ml.

15. The liquid pharmaceutical formulation of claim 13, wherein the exendin (9-39) or the pharmaceutically acceptable salt thereof is at a concentration of about 30 mg/ml.

16. The liquid pharmaceutical formulation of claim 13, wherein the exendin (9-39) or the pharmaceutically acceptable salt thereof is at a concentration of about 60 mg/ml.

17. The liquid pharmaceutical composition of claim 1, formulated for subcutaneous administration.

18. The liquid pharmaceutical formulation of claim 1, wherein the liquid pharmaceutical formulation, when administered to a human subject, exhibits a higher $C_{max}$ for exendin (9-39) than a composition comprising the same dose of exendin (9-39) or a pharmaceutical acceptable salt thereof formulated in 0.9% normal saline.

19. The liquid pharmaceutical formulation of claim 1, wherein the liquid pharmaceutical formulation, when administered to a human subject, exhibits a higher 12-hour AUC for exendin (9-39) than a composition comprising the same dose of exendin (9-39) or a pharmaceutical acceptable salt thereof formulated in 0.9% normal saline.

20. The liquid pharmaceutical formulation of claim 1, wherein the liquid pharmaceutical formulation, when administered to a human subject, exhibits a higher trough plasma concentration for exendin (9-39) than a composition comprising the same dose of exendin (9-39) or a pharmaceutical acceptable salt thereof formulated in 0.9% normal saline.

21. A method of treating or preventing hyperinsulinemic hypoglycemia in a subject, comprising administering to the subject the liquid pharmaceutical formulation of claim 1.

22. The method of claim 21, wherein the subject has previously had an upper-gastrointestinal procedure.

23. The method of claim 22, wherein the subject has previously had a bariatric procedure.

24. The method of any of claim 21, wherein the method comprises subcutaneously administering to the subject the liquid pharmaceutical formulation comprising exendin (9-39) at a dosage of about 30 mg to about 75 mg once daily (QD).

25. The method of claim 21, wherein the method comprises subcutaneously administering to the subject the liquid pharmaceutical formulation comprising exendin (9-39) at a dosage of about 30 mg, 45 mg, or 90 mg QD.

26. The method of claim 21, wherein the method comprises subcutaneously administering to the subject the liquid pharmaceutical formulation comprising exendin (9-39) at a dosage of about 15 mg, 30 mg, or 45 mg twice daily (BID).

27. The liquid pharmaceutical formulation of claim 13, wherein the exendin (9-39) or the pharmaceutically acceptable salt thereof is at a concentration of about 45 mg/ml.

28. The liquid pharmaceutical formulation of claim 13, wherein the exendin (9-39) or the pharmaceutically acceptable salt thereof is at a concentration of about 90 mg/ml.

29. The method of claim 21, wherein the method comprises subcutaneously administering to the subject the liquid pharmaceutical formulation comprising exendin (9-39) at a daily dosage of about 30 mg, 45 mg, or 90 mg.

30. The method of claim 29, wherein the method comprises subcutaneously administering to the subject the liquid pharmaceutical formulation comprising exendin (9-39) once per day (QD) or twice per day (BID).

* * * * *

UNITED STATES PATENT AND TRADEMARK OFFICE
CERTIFICATE OF CORRECTION

PATENT NO. : 11,020,484 B2
APPLICATION NO. : 16/461329
DATED : June 1, 2021
INVENTOR(S) : Xiaofeng Xiong et al.

Page 1 of 1

It is certified that error appears in the above-identified patent and that said Letters Patent is hereby corrected as shown below:

In the Claims

In Column 28, Line 53, Claim 1: delete "above"

Signed and Sealed this
Twenty-sixth Day of October, 2021

Drew Hirshfeld
*Performing the Functions and Duties of the*
*Under Secretary of Commerce for Intellectual Property and*
*Director of the United States Patent and Trademark Office*